United States Patent [19]
Mickle et al.

[11] Patent Number: 6,099,832
[45] Date of Patent: *Aug. 8, 2000

[54] TRANSPLANTS FOR MYOCARDIAL SCARS

[75] Inventors: Donald A. G. Mickle, Toronto; Ren-Ke Li, Scarborough; Richard D. Weisel, Toronto, all of Canada

[73] Assignee: Genzyme Corporation, Cambridge, Mass.

[*] Notice: This patent is subject to a terminal disclaimer.

[21] Appl. No.: 09/099,994

[22] Filed: Jun. 19, 1998

Related U.S. Application Data

[63] Continuation-in-part of application No. 08/863,882, May 28, 1997.

[51] Int. Cl.$^7$ .......................... A61K 35/34; C12N 15/09; C12N 15/85
[52] U.S. Cl. ...................... 424/93.21; 435/455; 435/325; 435/378
[58] Field of Search ............................... 435/325, 29, 34, 435/366, 373, 378, 360, 362, 371, 374, 395, 398, 403, 405; 424/400, 422, 93.1, 93.2, 93.21, 93.3, 93.7

[56] References Cited

U.S. PATENT DOCUMENTS

| | | | |
|---|---|---|---|
| 5,199,942 | 4/1993 | Gillis | 604/4 |
| 5,202,120 | 4/1993 | Silver et al. | 424/93 |
| 5,543,318 | 8/1996 | Smith et al. | 435/240.2 |
| 5,580,779 | 12/1996 | Smith | 435/378 |
| 5,602,301 | 2/1997 | Field | 800/8 |
| 5,733,727 | 3/1998 | Field | 435/6 |

FOREIGN PATENT DOCUMENTS

| | | |
|---|---|---|
| 95/14079 | of 0000 | WIPO . |
| WO 95/12979 | 5/1995 | WIPO . |
| WO 95/34581 | 12/1995 | WIPO . |
| WO 96/38544 | 12/1996 | WIPO . |

OTHER PUBLICATIONS

Chiu et al., *Ann. Thorac. Surg.* 60:12–18 (1995).
Gussoni et al., *Nature* 356:435–438 (1992).
Koh et al., *Journal of Clinical Investigation* 92:1548–1554 (1993).
Li et al., *J. Mol. Cell. Cardiol.*, 26:A162 (1994).
Li et al., *Cardiovascular Res.* 32:362–373 (1996).
Li et al., *Ann. Thorac. Surg.* 62:654–661 (1996).
Li et al., *J. Tiss. Cult. Meth.*, 14:93–100 (1992).
Soonpaa et al., *Science* 264:98–101 (1994).
Thompson et al., *Science* 257:868–870 (1992).
Leor et al., "Transplantation of Fetal Myocardial Tissue Into the Infarcted Myocardium of Rat, A Potential Method for Repair of Infarcted Myocardium?" *Circulation* 94:(Supplement II) II–332 – II–336 (1996).
Li et al., "In Vivo Survival and Function of Transplanted Rat Cardiomyocytes" *Circulation Research* 78:283–288 (1996).
Murry et al., "Skeletal Myobalst Transplantation for Repair of Myocardial Necrosis" *J. Clin. Invest.* 98:2512–2523 (1996).
International Search Report for International Application No. 98/00520 dated Oct. 9, 1998.

*Primary Examiner*—George C. Elliott
*Assistant Examiner*—Jon Shuman
*Attorney, Agent, or Firm*—Clark & Elbing, LLP

[57] ABSTRACT

A method is provided for forming a graft in heart tissue which comprises the transplantation of cells chosen from cardiomyocytes, fibroblasts, smooth muscle cells, endothelial cells and skeletal myoblasts. The grafts are especially useful in treating scar tissue on the heart.

23 Claims, 16 Drawing Sheets

TRANSPLANTS FOR MYOCARDIAL SCARS

CROSS REFERENCE TO RELATED APPLICATION

This application is a continuation-in-part of U.S. Ser. No. 08/863,882, filed May 28, 1997.

FIELD OF THE INVENTION

The present invention relates to novel methods of cell transplantation into scar tissue in the heart in order to improve heart function, stimulate angiogenesis, and to salvage myocardium. The invention also relates to the preparation and culturing of the subject cells prior to transplantation, a mechanism for the delivery of gene therapy using such transplants, and to grafts comprising such cells.

BACKGROUND OF THE INVENTION

Organ transplantation and surgical resection have been used to replace or remove diseased non-functional myocardial tissue. Recently, fetal cellular transplantation has been used to improve neurological deficiencies found in Parkinson's disease (Tompson, L. et al., Science 257:868–870, 1992). In a similar approach, normal myoblasts have been transplanted into the skeletal muscle of patients with Duchenne muscular dystrophy (Gussoni, E. et al., Nature 356:435–438, 1992), where the transplanted cells expressed dystrophin.

Fetal ventricular cardiomyocytes, atrial tumor cells, and skeletal myoblasts have been transplanted into normal myocardium (Koh, GY et al., Journal of Clinical Investigation 92:1548–54, 1993; Soonpaa, MH et al., Science 264:98–101, 1994; U.S. Pat. No. 5,602,301). In the studies described in these references, the cells were transplanted into the middle and thickest layer of the heart, composed of cardiac muscle, which has an excellent blood supply. Transplanted atrial tumor cells formed intercalated disc junctions with the host cardiomyocytes. Myocardial function was not assessed.

Cardiac scar tissue is formed after the ventricular wall of the heart necroses due to damage. In contrast to myocardial tissue, cardiac scar tissue contains no cardiac muscle cells. Instead, it is composed of connective tissue cells, such as fibroblasts, and non-cellular components, such as collagen and fibronectin. Cardiac scar tissue is non-contractile, and, therefore, interferes with normal cardiac function. Mature scar tissue is thought to be an inert tissue having a limited blood supply. Accordingly, the prior art suggests that cultured cells could not be successfully transplanted into mature scar tissue.

Scar tissue is much thinner than normal myocardium. In the method taught by Field in U.S. Pat. No. 5,602,301, cellular grafts are introduced into the myocardium by injection. However, this method, if applied to the much thinner scar tissue, would result in tissue ballooning and an accompanying increase in pressure within the region of cell injection. As a result, the transplanted cellular material would leak from the puncture point of the injection needle upon withdrawal, and the efficiency of such transplants would be reduced.

Thus, there is a need to develop cellular allo- or autotransplantation technology within scar tissue of the diseased myocardium to improve contractile function, minimize myocardial remodeling, stimulate angiogenesis, deliver gene therapy, rebuild the heart, and salvage damaged cardiomyocytes. The present invention addresses these needs.

SUMMARY OF THE INVENTION

It is an object of the present invention to provide cell transplantation methods for treating scar tissue in the myocardium which overcome deficiencies in the prior art. The invention illustrates that atrial myocytes, smooth muscle cells, endothelial cells, and fibroblasts can be successfully transplanted into the scar tissue formed after ventricular necrosis and into tissue membranes and porous synthetic membranes. The cell grafts form tissue that survived the three month duration of the study, improved myocardial function, limited myocardial remodeling, and stimulated angiogenesis. The presence of the grafts did not induce overt cardiac arrhythmias. When auto-cell transplantation occurred, immunorejection did not occur.

In a first aspect, the invention features a method of forming a stable myocardial graft in a mammal comprising, transplanting cells into myocardial tissue or scar tissue in the heart. Cells are chosen from the group consisting of: adult cardiomyocytes, fetal cardiomyocytes, pediatric cardiomyocytes, adult fibroblasts, fetal fibroblasts, smooth muscle cells, endothelial cells, and skeletal myoblasts.

In preferred embodiments of the first aspect of the invention, cells may be chosen from adult or fetal smooth muscle cells and fibroblasts, adult cardiomyocytes and endothelial cells may be co-transplanted, adult cardiomyocytes may be derived from atrial tissue, the graft may be derived from auto-, allo- or xenotransplantation, and the graft may comprise adult cardiomyocytes derived from autotransplantation, such as cardiomyocytes derived from atrial tissue.

In another preferred embodiment of the first aspect of the invention, the cells may be directly introduced into the myocardial tissue or the scar tissue, for example, by injection, and the injection site may be sealed with a biological adhesive to prevent leakage of the cells.

In other preferred embodiments of the first aspect of the invention the cells may be suspended on a biodegradable or non-degradable mesh, or may be transfected to deliver recombinant molecules to the myocardial tissue or the scar tissue.

In still another embodiment of the first aspect of the invention, the cells may be used in myocardial reconstructive surgery, and may be attached to the outer surface of the myocardial tissue or the scar tissue with a biological adhesive, or may be transplanted following an inflammatory response in the myocardial tissue. In addition, growth factors may be co-transplanted with the cells. Growth factors are chosen from the group consisting of: insulin-like growth factors I and II; transforming growth factor-β1, platelet-derived growth factor-B, basic fibroblast growth factor, and, vascular endothelial growth factor.

In yet other preferred embodiments of the first aspect of the invention, the cells are transplanted into scar tissue, and at least 10%, 20%, or 30% of the scar tissue area is occupied by transplanted cells four weeks after transplantation.

In a second aspect, the invention features a therapeutic graft for application in mammalian myocardial tissue or scar tissue in the heart, comprising transplanted cells chosen from the group consisting of: adult cardiomyocytes, pediatric cardiomyocytes, fetal cardiomyocytes, adult fibroblasts, fetal fibroblasts, adult smooth muscle cells, fetal smooth muscle cells, endothelial cells, and skeletal myoblasts.

In preferred embodiments of the second aspect of the invention, the graft may comprise adult cardiomyocytes and endothelial cells, the transplanted cells may be chosen from smooth muscle cells and fetal fibroblasts, the adult cardiomyocytes may be derived from atrial tissue, or the graft may be derived from auto-, allo- or xenotransplantation. The graft may comprise adult cardiomyocytes derived from autotransplantation and the cardiomyocytes may be derived from atrial tissue. The cells of the graft may be introduced into myocardial tissue or scar tissue by injection, and the cells may be transfected to deliver recombinant molecules to myocardial tissue or scar tissue. The graft may further comprise growth factors, for example, insulin-like growth factors I and II, transforming growth factor-β1, platelet-derived growth factor-B, basic fibroblast growth factor, and, vascular endothelial growth factor. Cells of the graft also may be suspended on a mesh (e.g., a biodegradable mesh).

In a third aspect, the invention features a therapeutic graft, for implantation into mammalian myocardial tissue or scar tissue in the heart, comprising a suitable biodegradable or non-biodegradable scaffolding having cells supported thereon. The cells are chosen from the group consisting of: adult cardiomyocytes, pediatric cardiomyocytes, fetal cardiomyocytes, adult fibroblasts, fetal fibroblasts, smooth muscle cells (e.g, adult smooth muscle cells or fetal smooth muscle cells), endothelial cells, and skeletal myoblasts.

In preferred embodiments of the third aspect of the invention, adult cardiomyocytes may be derived from atrial tissue, and the graft may comprise adult cardiomyocytes and adult endothelial cells. The graft may be used in cardiomyoplasty. The scaffolding of the graft may comprise Dacron or polyglycolic acid polymers with or without polylactic acid polymers, the cellular material may consist of cardiomyocytes, smooth muscle cells or endothelial cells, and the graft may further include an implantable pacemaker.

Grafts according to the third aspect of the invention may be used for closing cardiac defects, and for myocardial reconstructive surgery.

In a fourth aspect, the invention features a method of culturing cardiomyocytes from pediatric mammalian myocardial tissue comprising: a) comminuting said myocardial tissue; b) digesting said tissue for 15 minutes in a digesting solution containing 0.2% trypsin and 0.1% collagenase dissolved in phosphate buffered saline and separating the digested tissue solution from the remaining myocardial tissue; c) adding to the digested tissue solution a culture medium comprising Iscove's modified Dulbecco's medium (IMDM), 10% fetal bovine serum, and 0.1 mM β-mercaptoethanol; culture medium being added in a ratio of 20 volumes of culture medium to 1 volume of digesting solution; d) centrifuging the resulting solution at 581×g for 5 minutes and discarding the supernatant; e) re-suspending the pellet in fresh culture medium; f) culturing the suspension in 10% fetal bovine serum and 0.1 mM β-mercaptoethanol; and, g) isolating cardiomyocytes from the culture.

In preferred embodiments of the fourth aspect of the invention the method may further include passaging cardiomyocytes by sub-culturing with a sub-culturing enzyme solution comprising 0.01% trypsin, 0.02% glucose, and 0.5 mM EDTA. The method of the fourth aspect may further include storing the cardiomyocytes by a) dissociating cultured cardiomyocytes from the culture plate using sub-culturing enzyme solution; b) adding culture medium in a ratio of 5 volumes of culture medium to 1 volume of sub-culturing enzyme solution; c) centrifuging the solution at 581×g for 5 minutes; d) discarding the supernatant and re-suspending the pellet in 1 mL IMDM containing 20% fetal bovine serum and 20% glycerol; and, e) freezing and storing the resulting suspension in liquid nitrogen. The method may further include thawing the frozen sample at 37° C. and culturing the cardiomyocytes for 3 to 5 days in a solution of IMDM containing 20% fetal bovine serum.

In a fifth aspect, the invention features a method of culturing cardiomyocytes from adult mammalian myocardial tissue comprising: a) comminuting said myocardial tissue; b) digesting the tissue for 15 minutes in a digesting solution containing 0.2% trypsin and 0.1% collagenase dissolved in phosphate buffered saline; c) separating the digested tissue solution and digesting the remaining tissue with fresh digesting solution for 10 minutes; d) combining both digested tissue solutions from steps (b) and (c) and adding a culture medium comprising Iscove's modified Dulbecco's medium (IMDM, containing 10% fetal bovine serum, and, 0.1 mM β-mercaptoethanol) in a ratio of 20 volumes of culture medium to 1 volume of said digesting solution; e) centrifuging the resulting solution at 581×g for 5 minutes and discarding the supernatant; f) re-suspending the pellet in fresh culture medium; g) culturing the suspension in 10% fetal bovine serum and 0.1 mM β-mercaptoethanol; and, h) isolating cardiomyocytes from the culture.

In a preferred embodiment of the fifth aspect of the invention, the method may further include passaging the cardiomyocytes using sub-culturing enzyme solution comprising 0.01% trypsin, 0.02% glucose, and 0.5 mM EDTA.

The method of the fifth aspect also may further include storing cardiomyocytes by a) dissociating cultured cardiomyocytes from the culture plate using sub-culturing enzyme solution; b) adding culture medium in a ratio of 5 volumes of culture medium to 1 volume of sub-culturing enzyme solution; c) centrifuging the solution at 581×g for 5 minutes; d) discarding the supernatant and re-suspending the pellet in 1 mL IMDM containing 20% fetal bovine serum and 20% glycerol; and, e) freezing and storing the resulting suspension in liquid nitrogen.

In another embodiment of the fifth aspect, the method may further include thawing the frozen sample at 37° C. and culturing the cardiomyocytes for 3 to 5 days in a solution of IMDM containing 20% fetal bovine serum.

In a sixth aspect, the invention features a method of treating defective, damaged or scarified heart tissue, comprising transplanting into the tissue a graft of cells chosen from the group consisting of: adult cardiomyocytes, pediatric cardiomyocytes, fetal cardiomyocytes, adult fibroblasts, fetal fibroblasts, adult smooth muscle cells, fetal smooth muscle cells, endothelial cells, and skeletal myoblasts.

In preferred embodiments of the sixth aspect of the invention, the adult cardiomyocytes may be derived from atrial tissue, cells in the graft may be adult cardiomyocytes and endothelial cells, the cells may be directly introduced into heart tissue, and the graft may be a patch comprising cells suspended on a biologically acceptable biodegradable or non-biodegradable scaffolding.

In still other preferred embodiments of the sixth aspect of the invention, the cells are transplanted into scar tissue, and at least 10%, 20%, or 30% of the scar tissue is occupied by transplanted cells four weeks after transplantation.

In another preferred embodiment of the sixth aspect of the invention, the method may comprise the steps of: (a) surgically removing defective heart tissue thereby creating an opening; and, (b) attaching the graft to the opening to form a water tight seal.

In a seventh aspect, the invention features isolated cells for transplantation into myocardial scar tissue, selected from the group consisting of: adult cardiomyocytes, pediatric cardiomyocytes, adult fibroblasts, fetal fibroblasts, adult smooth muscle cells, fetal smooth muscle cells, endothelial cells, and skeletal myoblasts, wherein the cells survive in myocardial scar tissue after transplantation and improve cardiac function, relative to cardiac function of a heart having similar myocardial scar tissue that is not transplanted with cells. Cardiac function is assessed by at least one of the criteria in the group consisting of: area occupied by scar tissue; vascularization of scar tissue; blood flow to scar tissue; developed pressure, systolic pressure; end diastolic pressure; and dp/dt.

In preferred embodiments of the seventh aspect of the invention, the cells may comprise at least two of the cell types selected from the group. For example, the cells may comprise a combination of: adult cardiomyocytes and endothelial cells; pediatric cardiomyocytes and endothelial cells; or myoblasts and endothelial cells.

In an eighth aspect, the invention features a method for testing a pharmacological agent that is intended to prevent or ameliorate cardiac damage during cardiac surgery. The method comprises exposing the pharmacological agent to isolated cells selected from the group consisting of: adult cardiomyocytes, pediatric cardiomyocytes, adult fibroblasts, fetal fibroblasts, adult smooth muscle cells, fetal smooth muscle cells, endothelial cells, and skeletal myoblasts, wherein the cells survive in myocardial scar tissue after transplantation and improve cardiac function, relative to cardiac function of a heart having similar myocardial scar tissue that is not transplanted with cells (cardiac function is assessed by at least one of the criteria in the group consisting of: area occupied by scar tissue; vascularization of scar tissue; blood flow to scar tissue; developed pressure, systolic pressure; end diastolic pressure; and dp/dt), wherein cells exposed to the pharmacological agent prevent or ameliorates cardiac damage during cardiac surgery, compared to cells not exposed to the pharmacological agent.

In an ninth aspect, the invention features a method of forming a stable cardiac graft in a mammal, comprising transplanting into the scar tissue of a heart, cells chosen from the group consisting of: adult cardiomyocytes; pediatric cardiomyocytes; adult fibroblasts; fetal fibroblasts; adult smooth muscle cells; fetal smooth muscle cells; endothelial cells; and skeletal myoblasts, wherein the cells survive in scar tissue in a heart after transplantation into scar tissue, and wherein the cells improve cardiac function, relative to cardiac function of a heart having similar myocardial scar tissue that is not transplanted with such cells, wherein cardiac function is assessed by at least one of the criteria in the group consisting of: area occupied by scar tissue; vascularization of scar tissue; blood flow to scar tissue; developed pressure, systolic pressure; end diastolic pressure; and dp/dt, wherein at least 10% of scar tissue is occupied by transplanted cells four weeks after transplantation.

In other embodiments of the ninth aspect of the invention, at least 20% or at least 30% of the scar tissue may be occupied by transplanted cells four weeks after transplantation, or at least 40% or at least 50% of the scar tissue may be occupied by transplanted cells eight weeks after transplantation.

In preferred embodiments of the ninth aspect, the cells may include at least two types of cells selected from the group. For example, the cells may comprise a combination of: adult cardiomyocytes and endothelial cells; pediatric cardiomyocytes and endothelial cells; or myoblasts and endothelial cells.

In other preferred embodiments of the ninth aspect of the invention, growth factors are co-transplanted with the cells. The growth factors are chosen from the group consisting of: insulin-like growth factors I and II; transforming growth factor-β1; platelet-derived growth factor-B; basic fibroblast growth factor; and, vascular endothelial growth factor.

In a tenth aspect, the invention features a method of treating defective, damaged or scarified heart tissue, comprising transplanting into defective, damaged or scarified heart tissue a graft of cells, wherein the graft of cells comprises a combination of: adult cardiomyocytes and endothelial cells; pediatric cardiomyocytes and endothelial cells; or myoblasts and endothelial cells.

In preferred embodiments of the tenth aspect of the invention, the graft may be used for cardiomyoplasty, for closing cardiac defects, or for myocardial reconstructive surgery.

In an eleventh aspect, the invention features a therapeutic graft for implantation in mammalian myocardial tissue or scar tissue in a heart, comprising biodegradable or non-biodegradable scaffolding supporting cells, wherein the cells consist of a combination of:

adult cardiomyocytes plus endothelial cells; pediatric cardiomyocytes plus endothelial cells; or myoblasts plus endothelial cells.

In various embodiments of the eleventh aspect of the invention, the scaffolding comprises Dacron or polyglycolic acid polymers with or without polylactic acid polymers, or further includes an implantable pacemaker.

In another embodiment of the eleventh aspect, the cells may be transfected to deliver recombinant molecules to the myocardial tissue or scar tissue.

In still another embodiment of the eleventh aspect, the graft may comprise growth factors, for example: insulin-like growth factors I and II; transforming growth factor-β1; platelet-derived growth factor-B; basic fibroblast growth factor: and, vascular endothelial growth factor.

In yet another embodiment of the eleventh aspect, the cells may be suspended on a biodegradable mesh.

BRIEF DESCRIPTION OF THE DRAWINGS

These and other features of the present invention will become more apparent in the following detailed description wherein references are made to the following figures.

DETAILED DESCRIPTION OF THE PREFERRED EMBODIMENTS

Figure 1:
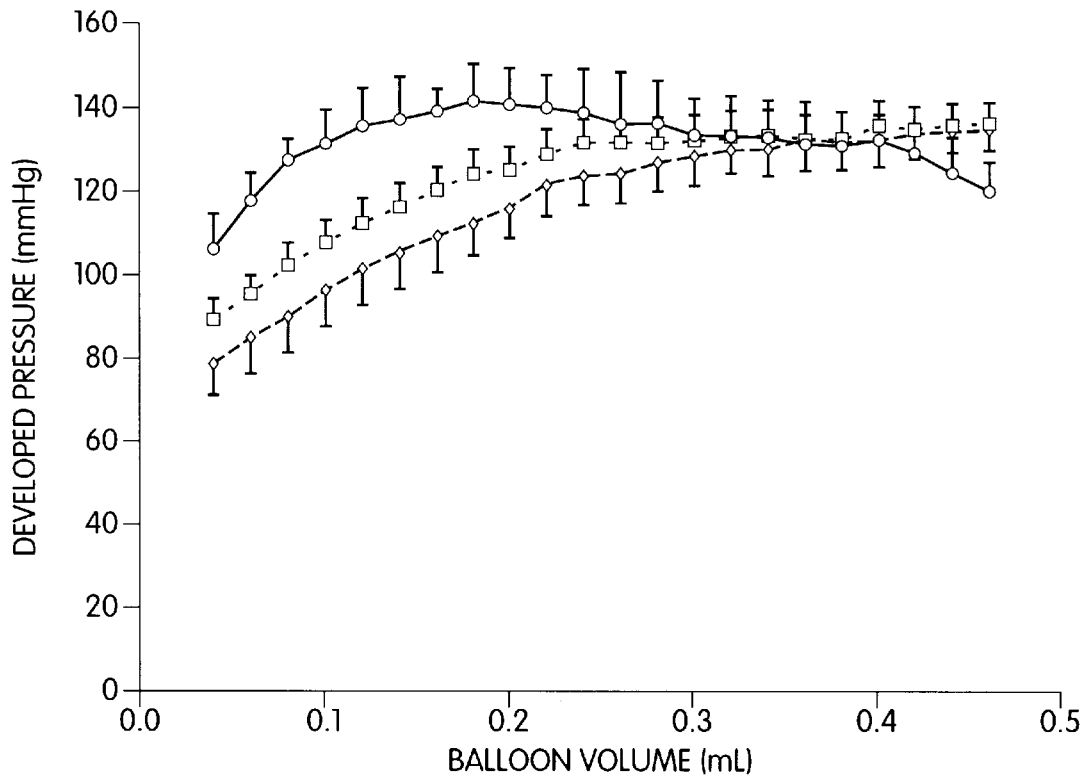
FIG. 1 is a graph showing the improvement in myocardial function of scarred hearts having smooth muscle cells transplanted into the scars.

We have discovered methods for improving the outcome of patients having myocardial scars. Our discovery was made while investigating the use of grafts, comprising cellular transplants, for treating scar tissue in the heart. We transplanted cultured cells into the center of a mature ventricular scar so that there was no contact between the transplanted cells and the host cells. Such methodology was followed to aid in the identification of the transplant. Initially, in transplanting fetal cardiomyocytes into the mature scar, it was surprising to find stimulation of angiogenesis in the affected area and an improvement in heart function. Since we were previously unsuccessful in transplanting adult ventricular cardiomyocytes into myocardial scar tissue, we were surprised that adult atrial cardiomyocytes could be successfully transplanted into such scar tissue. In further studies, we have transplanted auto- and allo-smooth muscle cells, fibroblasts, and endothelial cells into the center of a mature ventricular scar. As with our previous findings, the cell transplants formed stable grafts in the scar, improved myocardial function, decreased myocardial remodeling, stimulated angiogenesis, salvaged myocardium, and provided a means of gene delivery. On the basis of these studies we expect that similar results can be obtained from the use of skeletal myoblasts as well.

We have also developed a novel method for culturing, passaging and storing postnatal (adult or pediatric) human ventricular cardiomyocytes. Transplantation of cultured postnatal cardiomyocytes provides an approach for restoring function and blood flow to regions of the heart that are destroyed by acquired heart disease or are absent because of congenital heart disease. The postnatal cardiomyocyte cell culture method further provides a model for testing a variety of pharmacological or other approaches for preventing or ameliorating cardiac damage during cardiac surgery. Therefore, this unique method offers the promise of preventing injury as well as restoring heart function after cardiac injury.

The following examples will assist those skilled in the art to better understand the invention and its principles and advantages. It is intended that these examples be illustrative of the invention and not limit the scope thereof.

GENERAL METHODS

A) CELL ISOLATION, CULTURE, AND IDENTIFICATION

The following procedures were approved by the hospital's Experimentation Committee.

1. Fetal Rat Cardiomyocyte Cultures: Fetal rat cardiomyocytes were isolated using an enzymatic digestion method (Li, R-K et al., *Circulation Research* 78:283–288, 1996; Li, R-K et al., *Annals of Thoracic Surgery* 62:654–661, 1996) from 18-day gestational Sprague-Dawley rat heart ventricles (Charles River Canada Inc. Quebec, Canada). Fetal rats were anesthetized with intraperitoneal injection of sodium pentobarbital (30 mg/kg) and the hearts were then excised. The heart tissues were washed with phosphate-buffered saline (NaCl 136.9 mM, KCl 2.7 mM, $Na_2HPO_4$ 8.1 mM, $KH_2PO_4$ 1.5 mM, pH 7.3). The tissues were minced and incubated in 10 ml phosphate buffered saline containing 0.2% trypsin, 0.1% collagenase, and 0.02% glucose for 30 minutes at 37° C. The cardiomyocytes were then isolated by repetitive pipetting of the digested myocardial tissue. The cells in the supernatant were transferred to a tube containing 20 ml of cell culture medium (Iscove's modified Dulbecco's medium containing 10% fetal bovine serum, 0.1 mmole/L β-mercaptoethanol, 100 units/ml penicillin and 100 ug/ml streptomycin). The tube was centrifuged at 600×g for 5 minutes at room temperature and the cell pellet was resuspended in the cell culture medium for purification by plating (see Section 10 below).

2. Adult Rat Ventricular Cardiomyocyte Cultures: Adult rats (Charles River Canada Inc. Quebec, Canada) were anesthetized with intramuscular administration of ketamine hydrochloride (22 mg/kg body weight) followed by an intraperitoneal injection of sodium pentobarbital (30 mg/kg) and the hearts were then excised. Cardiomyocytes were isolated by enzymatic digestion as described in Section 1. Adult human ventricular biopsies obtained from the operating theatre were similarly enzymatically digested.

3. Adult Rat Atrial Cardiomyocyte Cultures: Adult rats weighing 400 g (Charles River Canada Inc. Quebec, Canada) were anesthetized as in Section 2 above. The atrial appendages were ligated and removed (rats survive this procedure), after which the atrial tissue was used for cardiomyocyte isolation as described in Section 1. Adult human atrial tissue was obtained from the operating theatre and similarly enzymatically digested.

4. Fetal Rat Smooth Muscle Cells: Fetal rat smooth muscle cells were isolated from 18-day gestational Sprague-Dawley rat stomachs by enzymatic digestion (Li, R-K et al., *Journal of Tissue Culture and Methods* 14:93–100, 1992). Fetal rats (Charles River Canada Inc. Quebec, Canada) were anesthetized with pentobarbital (30 mg/kg body weight, intraperitoneal) and the stomachs were then excised. The stomachs were washed with phosphate buffered saline, minced, and incubated in 10 ml phosphate buffered saline containing 0.2% trypsin, 0.1% collagenase, and 0.02% glucose for 30 minutes at 37° C. Smooth muscle cells were isolated by repetitive pipetting of the digested stomach tissue. The cells in the supernatant were transferred to a tube containing 20 ml of cell culture medium (199 medium containing 20% fetal bovine serum, 100 units/ml penicillin and 100 ug/ml streptomycin), and centrifuged at 600×g for 5 minutes at room temperature, after which the cells were resuspended in the cell culture medium and cultured.

5. Adult Rat Smooth Muscle Cells: Adult female rats (Charles River Canada Inc. Quebec, Canada) were anesthetized as described in Section 2 above. Uteri were removed after occlusion of blood vessels and incision was closed. Smooth muscle cells were isolated from uterus as described in Section 4.

6. Fetal Rat Fibroblasts: Fetal rat skin biopsies were obtained from anesthetized 18-day gestational Sprague-Dawley rats, and fibroblasts from fetal rat skin were isolated, purified and cultured as previously described (Mickle et al., *Journal of Molecular and Cell Cardiology* 22:1297–1304, 1990). Briefly, the tissue was washed with phosphate buffered saline, minced, and digested for 30 minutes at 37° C. in 10 ml phosphate buffered saline containing 0.2% trypsin, 0.1% collagenase, and 0.02% glucose. Fibroblasts were isolated by repetitive pipetting of the digested skin tissue. The cells in the supernatant were transferred into a tube containing 20 ml of cell culture medium (Dulbecco's Modified Essential Medium containing 10% fetal bovine serum, 100 units/ml penicillin and 100 ug/ml streptomycin) and centrifuged at 600×g for 5 minutes at room temperature, after which the cells were resuspended in the cell culture medium and cultured.

7. Adult Rat Fibroblasts: Skin biopsies were obtained from anesthetized adult Sprague-Dawley rats. Fibroblasts were isolated and cultured as described in Section 6.

8. Adult Rat Endothelial Cells: Adult rat vascular endothelial cells were isolated from Sprague-Dawley rat aorta by enzymatic digestion (Mickle et al., *Journal of Molecular and Cell Cardiology* 22:1297–1304, 1990). Adult rats (Charles River Canada Inc. Quebec, Canada) were anesthetized as described in Section 2. Aortas were excised, washed with phosphate buffered saline, incubated for 30 minutes at 37° C. in 10 ml phosphate buffered saline containing 0.2% trypsin, 0.1% collagenase, and 0.02% glucose, and washed with cell culture medium (199 medium containing 20% fetal bovine serum, 100 units/ml penicillin and 100 ug/ml streptomycin), after which the isolated endothelial cells were cultured.

9. Human Cell Isolation, Culturing and Storage: Human cardiomyocytes were isolated from atrial appendages and ventricular myocardial biopsies obtained from patients undergoing corrective cardiac surgery. Human myocardium was dissected to remove connective tissue and then minced to pieces less than 1 $mm^3$ in size.

9(a). Pediatric Cardiomyocytes: Pediatric tissue was digested for 15 minutes in an enzymatic digestion solution containing 0.2% trypsin, 0.1% collagenase dissolved in phosphate-buffered saline (no calcium or EDTA was added). Culture medium containing Iscove's modified Dulbecco's medium (IMDM), 10% fetal bovine serum and 0.1 mM β-mercaptoethanol was added in a ratio of 20 volumes culture medium to 1 volume enyzmatic digestion solution. The cell suspension was centrifuged at 581 g for 5 minutes, after which the supernatant was discarded. The cell and tissue pellet was resuspended in culture medium, after which the isolated cells were cultured on a dish for 5 to 8 days. Cardiomyocytes that migrated from this culture were collected by a Pasteur pipette and cultured once again.

9(b). Adult Cardiomyocytes: In contrast to pediatric myocardium digestion, adult human myocardium was digested twice. The second digestion was necessary for the adult tissue due to the increased amount of connective tissue. After the first digestion (as described in Section 9a), the cell suspension was collected, after which the tissue was re-digested for 10 minutes and the second cell suspension was collected. The two collected suspensions were combined, and centrifuged, after which the cells were resuspended and cultured. The digested tissue fragments in the pellet were collected and cultured for no longer than 2 days (to avoid cell deterioration) and a further enzymatic digestion carried out on the remaining undigested tissue if sufficient cells were not found in the suspensions. In addition, cardiomyocytes that migrated from the cultured tissue fragments were isolated and re-cultured.

9(c). Passaging of Cultures: The cardiomyocytes were cultured in a medium containing IMDM, 10% fetal bovine serum and 0.1 mM β-mercaptoethanol. The subculturing enzymatic solution for cell dissociation contained 0.01% trypsin, 0.02% glucose and 0.5mM EDTA. The cells were subcultured when the culture reached confluence (i.e. when the cell culture covered the dish surface and the cells began contacting each other). Cells that were subcultured before reaching confluency rapidly became de-differentiated. Such de-differentiated cells cannot be successfully transplanted. If the cells were allowed to become over-confluent, enzymatic digestion yielded cell clumps that would not dissociate. Cardiomyocytes in cell clumps did not divide in culture.

9(d). Storage of Cultured Cells: Primary cultures of human cardiomyocytes were dissociated from culture plates using the subculturing enzymatic digestion solution, after which culture medium was added in a ratio of 5 volumes culture medium to 1 volume digestion solution, and the cell suspension was centrifuged at 581 g for 5 minutes. The supernatant was removed and the cell pellet was gently re-suspended in 1 mL IMDM containing 20% fetal bovine serum and 20% glycerol, transferred to a sterile cryo-vial, and placed in a Nalgene freezing container containing isopropranol in its base. Cryo-vials were stored in a $-80°$ C. freezer container for a period of time that: (a) ensured that the cells reached $-80°$ C.; and (b) prevented over-oxidation of the cells. In the present example, cryo-vials were stored for a minimum of 4 hours and no longer than 8 hours. Cryo-vials containing the cells were placed in liquid nitrogen for long term storage.

9(e). Thawing of Cultures: When the stored cells were to be cultured, the vial was removed from liquid nitrogen and warmed at 37° C. Although 37° C. was preferred, cells were also thawed at other temperatures that allowed for rapid yet non-destructive warming. The initial plating of the cells was done in 10 ml of IMDM medium containing 20% fetal bovine serum (warming medium). Cells were kept in warming medium for 3 to 5 days to allow the cells to attach firmly to the culture dish before switching to the usual culture medium. The warming medium must contain IMDM and 20% fetal bovine serum. For example, if the warming medium contains 10% rather than 20% fetal bovine serum, the human cardiomyocytes will not divide and will de-differentiate. De-differentiated cardiomyocytes cannot be used for transplantation.

Cardiomyocytes that were cryo-frozen and warmed as described were successfully subcultured and were morphologically identical to cells that had not been frozen. Cells that had been frozen and cells that had not been frozen were analyzed for mitochondrial integrity at each passage for 7 passages (over the course of one month of subculture following thawing and plating). The mitochondrial enzyme cytochrome C oxidase showed no difference in activity between frozen and unfrozen cardiomyocytes at each passage. Our finding that primary human cardiomyocytes can be stored frozen and later revived allows their "lifetime" to be extended, thus enhancing the usefulness of such cells.

9(f). Endothelial Cells: Human vascular endothelial cells were isolated as described in section 8 from saphenous vein and aorta obtained from patients undergoing coronary bypass surgery.

9(g). Smooth Muscle Cells: Human smooth muscle cells were isolated from saphenous vein after endothelial cell isolation. After endothelial cells were collected from veins as described in Section 8, the tissue was minced and incubated in 10 ml phosphate buffered saline containing 0.2% trypsin, 0.1% collagenase, and 0.02% glucose for 30 minutes at 37° C. The smooth muscle cells were isolated by repetitive pipetting of the digested tissue. The cells in the supernatant were transferred into a tube containing 20 ml of cell culture medium (199 medium containing 20% fetal bovine serum, 100 units/ml penicillin and 100 ug/ml streptomycin), centrifuged at 600×g for 5 minutes at room temperature, resuspended in cell culture medium, and cultured.

9(h). Human Fibroblasts: Human fibroblasts were isolated from skin biopsies as described in Section 6.

10. Rat Cell Purification: Isolated rat cardiomyocytes, smooth muscle cells, vascular endothelial cells were purified by a preplating technique (Simpson et al., *Circulation Research* 51:787–801, 1982) which takes advantage of the finding that these cells require a longer time to attach to a cell culture dish than do fibroblast cells. Freshly isolated cells were plated on dishes and cultured for 2 hours at 37° C., after which the culture medium containing the suspended cells (minus the fibroblasts) was transferred into another dish for further culturing.

The other technique used for culture purification was the clonal dilution technique. When the cells are seeded at low density for culturing, viable cells form individual colonies. Any cell not of the desired type that is adjacent to a colony of interest is killed with a sterile needle. Desired colonies are then collected using a sterile Pasteur pipette, and transferred to new culture dishes for culturing and passaging.

Human cardiomyocytes were used without a purification step.

11. Cell Identification:

Cardiomyocytes: The purity of primary cultures of cardiomyocyte was assessed by immunofluorescent staining for cardiac myosin heavy chain (Rougier Bio-Tech Ltd, Quebec) (Li R-K, et al., *Cardiovascular Research* 32:362–73, 1996). The cultured cells were fixed with methanol at $-20°$ C. for 15 minutes, washed with phosphate buffered saline, incubated with a monoclonal antibody against cardiac myosin heavy chain for 45 minutes at 37° C., washed three times with phosphate buffered saline for 5 minutes each at room temperature, and then under humid and dark conditions incubated with rabbit anti-mouse IgG conjugated with fluorescein isothiocyanate for 45 minutes at 37° C. The cells were washed with phosphate buffered saline, mounted and photographed using a light and UV microscope. The purity of cardiomyocyte cultures was determined by counting the percentage of stained cells in 8 random fields/dish. Eight dishes of cardiomyocyte cultures were used in each cardiomyocyte preparation.

Smooth Muscle Cells: The purity of smooth muscle cell cultures was determined by immunofluorescent staining for α-smooth muscle cell actin (Sigma) as described in the previous paragraph.

Vascular Endothelial Cells: The purity of endothelial cell cultures was determined by immunofluorescent staining for factor VIII as described in the cardiomyocyte section above.

Fibroblasts: The purity of fibroblast cell cultures was determined by examining cell morphology with a microscope.

B) CELL TRANSPLANTATION

Subject animals were grouped into three categories: sham, control and transplantation. The criteria for such grouping was as follows:

| Group | Surgical exposure | Scar generation | Cell transplantation |
| --- | --- | --- | --- |
| Sham | X | | |
| Control | X | X | |
| Transplantation | X | X | X |

1. Surgical Exposure: Sprague-Dawley rats (500 gram) were anesthetized with ketamine (22 mg/kg body weight, intramuscular) followed by an intraperitoneal injection of pentobarbital (30 mg/kg body weight). Once anaesthetized, rats were intubated and positive pressure ventilation was maintained with a Harvard ventilator (Model 683, USA). The respiratory rate was set at 60 cycles/minute with a tidal volume of 2 ml. Animals were ventilated with oxygen-supplemented room air. The heart was exposed through a 2-cm left lateral thoracotomy. The muscle layer and skin incision were surgically closed with 5-0 vicryl sutures.

2. Myocardial Injury and Myocardial Scar Generation: The hearts of the adult rats were exposed as described in the previous paragraph. A 5-mm-diameter metal probe cooled to −190° C. for 2 minutes was applied to the left ventricular free wall of the heart for 20 seconds. This procedure was repeated 8 times. The muscle layer and skin incision were then surgically closed with 5-0 vicryl sutures.

The animals recovered from surgery in a warm environment, were monitored for 4 hours postoperatively and then given Penlog XL (benzathine penicillin G 150,000 U/ml and procaine penicillin G 150,000 U/ml) intramuscularly (0.25 ml/rat) every three days, and buprenorphine (0.01–0.05 mg/kg body weight) subcutaneously 8–12 hourly for the first 48 hours following surgery.

3. Transfection of the Cultured Cardiomyocytes: Freshly isolated or cultured cells were transfected by calcium phosphate coprecipitation (Shi Q-W, et al., *Journal of Molecular and Cell Cardiology* 24:1221–1229, 1992) with a plasmid containing the β-galactosidase gene. Plasmid DNA (20 ug) dissolved in 450 µl of sterile water and 50 µl of 2.5 M $CaCl_2$ was slowly added to 500 µl of aerated 2× HEPES-buffered saline (0.284 M NaCl, 0.050 M HEPES acid, and 1.48 mM $Na_2HPO_4$, pH 7.05). After 20 minutes at room temperature, the solution was added to a cardiomyocyte suspension ($1.0\times10^6$ cells/6 ml of culture medium). In the control groups the same procedure was performed either without plasmid DNA or with pREP4 (a plasmid that lacks a β-galactosidase gene; Invitrogen, USA; plasmid control). The cells were cultured at 37° C., 5% $CO_2$ and 95% air for 24 hours.

To determine the efficiency of cell transfection, cells cultured for either 24 hours or 4 weeks were washed three times with phosphate buffered saline, fixed in 2% formaldehyde and 2% glutaraldehyde in phosphate buffer (0.15 M NaCl and 0.015 M $NaH_2PO_4$, pH 7.2) at 4° C. for 5 minutes, washed with phosphate buffer containing 2.0 mM $MgCl_2$, and stained overnight at 37° C. in a solution containing 1 mg/ml 5-bromo-4-chloro-3-indolyl-beta-galactopyranoside (X-gal), 5 mM $K_3Fe(CN)_6$, 5 mM $K_4Fe(CN)_6 3H_2O$, 0.2 mM $MgCl_2$ in phosphate buffer (pH 7.2). The stained and non-stained cells in 8 random fields/dish (6 dishes from 6 preparations) were counted under the microscope to determine the percentage of cells containing β-galactosidase activity. Two dishes from each transplant experiment were used for a cell transfection efficiency study (N (number of animals)=6).

4. Cell Preparation and Transplantation: Cultured cells were washed three times with phosphate buffered saline to remove dead cells and then detached from the cell culture dish and each other with 0.05% trypsin in phosphate buffered saline for 3 minutes. After adding 10 ml of cultured medium, the cell suspension was centrifuged at 580×g for 3 minutes. The cell pellet was resuspended in culture medium at a concentration of $4\times10^6$ cells/ml culture medium. The volume of cell suspension was 0.25 ml for each cell transplantation.

On day 14 or 30 following myocardial scar generation (Section 2), the animals (which now had mature transmural scars in their ventricles) were anesthetized as described in Section 1. The scar tissue in the heart was exposed through a midline sternotomy. The cell suspension (0.25 ml) was injected into the scar tissue of the animals of the transplant group using a tuberculin syringe. Control animals were similarly injected with 0.25 ml of culture medium (no cells). The rats in the sham group underwent the surgical procedure without injection. Cryo-precipitate (fibrin glue) was placed on the injection sites to prevent leakage of the injected cells.

The chest was closed with 5-0 vicryl sutures. Antibiotics and analgesia were given as described in Section 1. Cyclosporin A, at a dose of 5 mg/kg body weight/day, was administered subcutaneously into animals of all three groups. The rats were housed in cages with filter tops.

C) MEASUREMENT OF HEART FUNCTION

Eight weeks after myocardial injury, the heart function of sham, control and transplanted animals was measured using a Langendorff preparation (Stephen SE, et al., *Annals of Thoracic Surgery* 59:1127–1133, 1995). The rats were anesthetized and heparin (200 units) was administered intravenously. The hearts were quickly isolated from rats and perfused in a Langendorff apparatus with filtered Krebs Heinseleit buffer (mmol/L NaCl 118, KCl 4.7, $KH_2PO_4$ 1.2, $CaCl_2$ 2.5, $MgSO_4$ 1.2, $NaHCO_3$ 25, glucose 11; pH 7.4) equilibrated with a 5% $CO_2$ and 95% $O_2$. A latex balloon was passed into the left ventricle through the mitral valve and connected to a pressure transducer (Model p10EZ, Viggo-Spectramed, Calif.) and transducer amplifier and differentiator amplifier (Model 11-G4113-01, Gould Instrument System Inc., Ohio). After 30 minutes of stabilization, coronary flow in the heart was measured in triplicate by timed collection in the emptying beating state. The balloon size was increased by addition of saline in 0.02 ml increments from 0.04 to 0.8 ml, or the volume at which end diastolic pressure reached to 30 mm Hg, or whichever came first. The systolic and diastolic pressures were recorded at each balloon volume and developed pressure was calculated as the difference between the systolic and diastolic pressures.

Hearts were weighed and their sizes were measured by water displacement.

D) MEASUREMENT OF LEFT VENTRICULAR REMODELING

The epicardial and endocardial surface areas of the normal and scar tissue in the left ventricular free wall (LVFW) were measured by the techniques of Pfeffer et al (Pfeffer JM, et al., *American Journal of Physiology* 260:H1406–14, 1991) and Jugdutt and Khan (Jugdutt BI, et al., *Circulation* 89:2297–307, 1994). Briefly, the hearts were fixed in distension (30 mm Hg) with 10% phosphate-buffered formalin solution and then cut into 3 mm thick sections. For each section, the area of normal tissue, scar tissue, and transplanted tissue in the left ventricular free wall were traced onto a transparency and quantified using computerized planimetry (Jandal Scientific Sigma Scan, USA) as described by Wu et al. (Wu TW, et al., *Cardiovascular Research* 27:736–39, 1993). The lengths of left ventricular free wall and scar tissue on both the endocardial and epicardial surfaces of each section were measured. The surface areas of the epicardial and endocardial scar tissue and left ventricular free wall were measured as:

(endocardial length+epicardial length)×section thickness (3 mm).

The surface area percentage of scar tissue in the left ventricular free wall (LVFW) was calculated as:

$$\frac{(\text{epicardial scar size} + \text{endocardial scar size})}{(\text{endocardial LVFW1} + \text{epicardial LVFW})} \times 100$$

To calculate the percentage of the surface area in the scar tissue occupied by the transplanted tissue, the following equation was used:

$$\frac{\text{(cardiac tissue length in the scar tissue of each section)} \times \text{(section thickness (3 mm))}}{\text{(total scar area)}} \times 100$$

E) HISTOLOGY AND ELECTRON MICROSCOPY OF TRANSPLANTED CELLS

On day 30 or 45 post-transplantation, the animals were anesthetized as in Example 1 and transplant, control, and sham hearts were exposed through a midline sternotomy and quickly harvested. The animals were euthanised by exsanguination under general anesthesia.

To localize the tissue formed by transplanted cells, the transplanted and control myocardial scar tissues were fixed in 5% glacial acetic acid in methanol. The tissue was embedded in paraffin and cut into 10 μm thick sections. After removal of the paraffin by immersing the sections for 3 minutes in xylene and then in 100, 95, 90, 85, and 70% ethanol for 3 minutes each, the samples were stained with haematoxylin and eosin as described by the manufacturer (Sigma Diagnostics, St. Louis, Mo.), and photographed.

To stain for β-galactosidase activity in the transplanted cardiomyocytes, the heart sections were fixed at 4° C. for 12 hours in 2% formaldehyde and 2% glutaraldehyde in phosphate buffer (0.15 M NaCl and 0.015 M NaH$_2$PO$_4$, pH 7.2). The transplanted cardiomyocytes were localized by staining for β-galactosidase activity as described earlier in Example 2. The stained tissue was embedded in paraffin and cut into 10 μm thick sections that were stained with haematoxylin and eosin as described in the last paragraph.

To identify cultured ventricular and atrial cardiomyocyte transplants, the transplanted heart tissue was immunofluorescently stained for cardiac myosin heavy chain. Briefly, tissue sections were washed three times with phosphate buffered saline and fixed with 2 ml 100% cold methanol at −20° C. for 15 minutes. After washing three times with phosphate buffered saline and drying by draining, the tissue sections were exposed for 45 minutes at 37° C. to monoclonal antibodies against cardiac myosin heavy chain (Rougier Bio-Tech, Montreal, Canada), diluted 1:20 with saline. Control tissues were incubated under the same conditions with phosphate buffered saline. The tissues were washed three times with phosphate buffered saline for 15 minutes at room temperature with gentle shaking, after which the secondary antibody, rabbit anti-mouse IgG conjugated with fluorescein isothiocyanate at a concentration of 1:32 dilution with phosphate buffered saline, was added. The tissues were incubated with the second antibody under dark and humid conditions for 45 minutes at 37° C. After washing with phosphate buffered saline, the cells in the transplant control tissues were visualized under ultraviolet light using an epi-microscope with a blue filter.

The smooth muscle cell transplants were identified by staining immunofluorescently using a monoclonal antibody for α-smooth muscle actin as the primary antibody. Endothelial cell transplants were identified by immunofluorescent staining for factor VIII, as described in the next section.

Fibroblast transplants were identified by the presence of a localized immunorejection within the ventricular scar.

F) HISTOLOGICAL AND ELECTRON MICROSCOPY STUDIES OF ANGIOGENESIS IN THE GRAFT

For immunocytochemical staining of factor VIII-related antigen in the vascular endothelial cells, tissue sections processed as in Section E above were incubated with xylene twice for 5 minutes each, 100% ethanol twice for 2 minutes each and then with 70% ethanol twice for 1 minute each. The sections were incubated with rabbit IgG against factor VIII-related antigen (Dimension Lab. Inc., Ontario). The control samples were incubated with phosphate buffered saline under the same conditions. The test and control samples were incubated with goat anti-rabbit IgG conjugated with peroxidase. After washing the samples three times with phosphate buffered saline following secondary antibody staining, the samples were immersed in diaminobenzidine-H$_2$O$_2$ (2 mg/ml diaminobenzidine, 0.03% H$_2$O$_2$ in 0.02 M phosphate buffer) solution for 15 minutes. The samples were washed with phosphate buffered saline. The stained vascular endothelial cells in the grafts (N=17) and control groups (N=14) were counted using a light microscope at 200× magnification. The result was expressed as number of blood vessels/field area (0.8 mm2).

For electron microscopy studies, hearts were fixed in 1% glutaraldehyde in phosphate buffer, postfixed with 1% osmium tetroxide, dehydrated in graded ethanol (50, 70, 90 and 100%), polymerized in propylene oxide at 60° C. overnight, sectioned, and examined using a JEOL 1200 TEM electron microscope (Li R-K, et al., *Cardiovascular Research* 32:362–73, 1996).

G) CELL GRAFTS

Cultured cardiomyocytes, smooth muscle cells, endothelial cells, and/or fibroblasts were seeded onto biological mesh, such as a collagen membrane, and on non-biological membranes, such as non-degradable membranes (Dacron) or degradable membranes (polyglycolic acid polymers), and the mesh and cells were cultured in cell culture medium. Seven days after culture, the cell-containing mesh was fixed in 2% formaldehyde and 2% glutaraldehyde in phosphate buffer (0.15 M NaCl and 0.015 M NaH$_2$PO$_4$, pH 7.2) at 4° C. for 12 hours, embedded in paraffin, and cut into 10 μm thick sections, which were stained with haematoxylin and eosin as described in Section E, and photographed.

H) CELL GLUING TECHNIQUE FOR CELL TRANSPLANTATION

To be successful in preventing failure of the infarcted heart, sufficient cardiomyocytes must be implanted into the infarcted myocardium. Although this can be done by multiple syringe injections, injecting the cells, unfortunately, limits the number of cells which can be transplanted into myocardial scar tissue. We have investigated another technique to apply a large number of cells onto the infarcted myocardium. Thrombin and cryoprecipitate (fibrin glue), which are derived from human blood, clot rapidly. Our in vitro results showed survival and contraction of cardiomyocytes in fibrin clots. We used this fibrin glue for cell transplantation.

1. Gluing Injection Site to Prevent Transplanted Cell Leakage: The biological glue is applied onto the injection site while the injection needle is still in place. The needle is withdrawn after the glue clots. In such manner, leakage of transplanted cells, as discussed previously, is prevented.

2. Gluing the Cells onto the Myocardial Scar Tissue to Prevent Injection Damage: We removed the epicardium over the scar and damaged myocardium. The transplanted cells were suspended in thrombin, and the thrombin/cell suspension was applied onto the myocardial scar tissue with cryoprecipitate (fibrin glue). The glue caused the cell suspension to adhere to the surface of both the scarred and normal myocardium, after which the pericardium was glued on top of the fibrin clot. Cell loss was prevented. We found that glued cardiomyocytes can survive on the myocardial scar tissue and permit a large number of cells to be transplanted. This technique improved heart function better than only injecting the cells. The cardiomyocytes glued directly onto the myocardium without epicardium can connect with host cardiomyocytes and cardiomyocytes to contract synchronously with the host myocardium.

3. Gluing the Cellular Mesh onto the Myocardial Scar Tissue to Prevent Its Expansion: Cell grafts comprising biological or non-biological mesh having cells suspended thereon (as described in Example 7) were glued onto the scar tissue. The pericardium was in turn glued on top of the mesh.

I) DATA ANALYSIS

Data are expressed as the mean±standard error. The Statistical Analysis System software was used for all analysis (SAS Institute, Cary, N.C.). Comparisons of continuous variables between more than two groups were performed by a one-way analysis of variance. If the F ratio was significant from the analysis of variance, a Duncan's multiple-range t test was employed to specify differences between the groups. Alpha for these analyses was set at p<0.05.

Function data were evaluated for the sham, control and transplant groups by an analysis of covariance using intracavitary balloon volume as the covariate and systolic, diastolic and developed pressure as dependent variables. Main effects were group, volume, and the interaction between group×volume. If there was an overall difference in the analysis of covariance, multiple pair-wise comparisons were performed to specify which groups were different. Because there were multiple pair-wise comparisons, a Bonferroni correction was performed and the critical alpha level was set at 0.01 for the analysis of covariance.

J) USE OF GROWTH FACTORS IN TREATING IDIOPATHIC HYPERTROPHIC CARDIOMYOPATHY (HCM)

Idiopathic hypertrophic cardiomyopathy (HCM) is a primary cardiac abnormality characterized by regional asymmetrical myocardial hypertrophy. The hypertrophic myocardium can result in obstruction of left ventricular ejection as well as systolic and diastolic dysfunction and myocardial ischemia. Symptoms unresponsive to medical therapy can necessitate surgery.

HCM is described for the most part as a heterogeneous disease of the sarcomeres. At least 34 missense mutations have been described in the β-myosin heavy chain gene, and 7 mutations in candidate loci also exist. However, family studies suggest that the autosomal dominant trait accounts for only 50% of HCM patients. The remaining HCM patients show no familial transmission and the disease occurs sporadically. Myocardial calcium kinetics and sympathetic stimulation have been studied because of diastolic functional abnormalities. However, none of these findings explains the regional myocardial hypertrophy (cardiomyocyte hypertrophy and over production of extracellular matrix proteins) observed in most HCM patients. The etiology of this disease remains unknown. It is thought that growth factors may play an important role in cardiomyocyte proliferation, cell hypertrophy and the overproduction of extracellular matrix.

To investigate the involvement of growth factors in myocardial hypertrophy in HCM patients, we evaluated gene expression and cellular localization of transforming growth factor β1 (TGFβ1), insulin-like growth factors (IGF-I, -II), and platelet-derived factor-B (PDGF-B) in ventricular biopsies obtained from patients with HCM (N=8), aortic stenosis (AS, N=8), stable angina (SA, N=8), and explanted hearts with ischemic cardiomyopathy (TM, N=7).

Methods: Levels of TGFβ1, IGF-I, IGF-II and PDGF-B transcripts were quantitated using multiplex RT-PCR. Glyceraldehyde 3-phosphate dehydrogenase (G3PDH) was used as an internal standard. Antibodies against TGFβ1 and IGF-I were used to localize their peptides within the myocardium. Antisense and sense (control) cRNA probes for TGFβ1 and IGF-I, labeled with digoxigenin, were used to localize the growth factor transcripts by in situ hybridization.

Results: mRNA levels (densitometric ratio of GF/G3PDH) of TGFβ1 and IGF-I in HCM myocardium (0.75±0.05, 0.85±0.15, mean±1SE) were significantly (p<0.01 for all groups) elevated in comparison to non-HCM myocardium (AS: 0.38±0.07, 0.29±0.06; SA: 0.32±0.04, 0.18±0.05; TM: 0.25±0.03, 0.15±0.03). mRNA level of TGFβ1 and IGF-I in the hypertrophic AS myocardium were greater (p=0.02, p=0.05) than those in the explanted myocardium (TM). Immunohistochemical and in situ hybridization studies showed increased expression of TGFβ1 and IGF-I in the HCM cardiomyocytes.

Conclusion: Gene expression of TGFβ1 and IGF-I was enhanced in idiopathic hypertrophy and may be associated with its development.

RESULTS

1. Ventricular and Atrial Cardiomyocytes: Fetal and adult mammalian ventricular cardiomyocytes and adult mammalian atrial cardiomyocytes were isolated using enzymatic digestion as described above in Sections 1–3, Example I. After purification, the purity of the cultured ventricular and atrial cardiomyocytes was greater than 94% (N=8) as determined by the percentage of cells that stained for cardiac myosin heavy chain. The cardiomyocytes grew in vitro, connected with each other and formed a tissue pattern after six days of culture. The fetal cardiac-like tissue contracted regularly and spontaneously in culture. The adult cardiomyocytes did not contract in culture.

2. Smooth Muscle Cells: Fetal and adult smooth muscle cells were successfully cultured. The cells proliferated in the culture. The cultured cells were stained strongly with antibodies against α-smooth muscle actin.

3. Vascular Endothelial Cells: Endothelial cells were isolated from blood vessel and cultured. Staining with antibody against factor VIII showed that more than 95% cells in the culture dish were endothelial cells.

4. Fibroblasts: Fetal and adult skin fibroblasts were isolated and cultured. The cells proliferated in the culture condition. When the culture reached confluency, the cells formed a typical fibroblast pattern: spindle-shaped cells in a wave pattern.

5. Cell Transfection: Twenty-four hours after transfection of freshly isolated cells, the percentage of the transfected cells with β-galactosidase was 18.2±5.2% (N=6). No cells stained positively in the control groups with plasmid pREP4 (N=6) and without a plasmid (N=6). After culturing for 4 weeks, 5.4±3.1% (N=6) of the transfected cells stained positively for β-galactosidase activity.

6. Myocardial Scar Tissue: Immediately after myocardial injury, 25±3% of the left ventricular free wall (LVFW) was transmurally damaged. The cardiomyocytes were fragmented. At one week, most of the necrosed cardiomyocytes were gone and a predominantly mononuclear inflammatory infiltrate was present in the affected area. At two weeks the inflammatory infiltrate had almost disappeared and fibroblasts and collagen deposition were evident. At four and eight weeks, the scar was composed of fibrotic tissue. The tissue was less cellular and lymphocytes were not observed. No cardiac muscle cells were observed in any scar tissue.

The myocardial scar of the left ventricle increased in size over the 8 week study period in the control hearts. Although the scar sizes at 1 and 2 weeks (13±6% and 21±4% of left ventricular free wall) were not statistically different, the scar size after 4 weeks (39±5% of left ventricular free wall) was greater ($p<0.01$). At 8 weeks there was a further increase ($p<0.01$) in scar size (55±3% of left ventricular free wall).

7. Optimal Time for Cell Transplantation: The fetal rat cardiomyocytes transplanted into myocardial tissue immediately after myocardial damage did not survive in the affected area. The scar area (53±5%) of transplanted hearts was similar to that of the control group (55±3% of the left ventricular free wall). Cardiomyocytes transplanted at 2 weeks after myocardial damage formed cardiac tissue that occupied 34% of the total scar area (11±3% of the left ventricular free wall). Similarly, cardiomyocytes transplanted at 4 weeks occupied 32% of total scar area (14±4% of left ventricular free wall). The scar sizes in the hearts that received transplants 2 weeks and 4 weeks after myocardial damage were smaller ($p<0.01$) than the scar size of the control hearts. The scar size of the hearts that received transplants 2 weeks after myocardial damage was smaller ($p<0.01$) than that of the hearts that received transplants 4 weeks after myocardial damage.

8. Transplanted Cells in Myocardial Scar Tissue: Cells were transplanted into transmural scars two and four weeks after scar cryo-induction. Six weeks or four weeks after ventricular cardiomyocyte transplantation (i.e., eight weeks after scar induction in all animals), only fetal cardiomyocyte tissue (N=17) had formed within the myocardial scar tissue. The cells were connected to each other and formed a cardiac tissue pattern. The tissue of all 3 animals, transplanted with cardiomyocytes transfected with the β-galactosidase gene, contained β-galactosidase activity. The transplanted cardiomyocytes contained sarcomeres and were connected by junctions composed of desmosomes and fascia adherens, which were not present in the cardiomyocytes immediately prior to transplantation. Lymphocytic infiltration surrounded the cardiac tissue formed by transplanted fetal cardiomyocytes. In the control animals (N=14), cardiac tissue, lymphocytic infiltration, and β-galactosidase activity were not observed in the scar. The eight-week scar was less cellular than the four-week old scar tissue.

Adult rat atrial cardiomyocytes were autotransplanted into the scar tissue of the same rat. At 6 weeks after transplantation, the transplanted cells were detected in the myocardial scar tissue by staining with an antibody against cardiac myosin heavy chain. There was no lymphocytic infiltration. No cardiac tissue was found in the scar tissue of control rats.

At 6 weeks after transplantation, scars transplanted with either allo- or auto-smooth muscle cells contained smooth muscle tissue that stained positively for α-smooth muscle actin. The allotransplants were infiltrated with lymphocytes, indicative of immuno-rejection. In contrast, there was no lymphocytic infiltrate or signs of immunorejection in the auto-smooth muscle cell transplant.

FIG. 1 shows the improved cardiac function of scarred hearts transplanted with smooth muscle cells. Hearts were cryo-injured, after which the mature scar tissue was transplanted with allogenic smooth muscle cells. Function measurements were made four weeks after transplantation. The graph shows developed balloon pressures of is sham (top line; no cryo-injury, no transplantation), control (bottom line; cryo-injury, no transplantation), and transplanted (middle line) hearts with increasing balloon volumes. Developed pressures of transplanted hearts were significantly higher than control hearts ($p=0.0001$), but lower than that sham of sham hearts ($0=0.0001$).

At 6 weeks after transplantation, the transplanted fibroblasts proliferated in the myocardial scar tissue. The cells secreted extracellular matrix, which increases the thickness of the scar tissue. The transplanted cells also stimulated angiogenesis (see below), which survived damaged myocardial tissue in the scar tissue. There were no cardiac muscle cells in the scar tissue in control animals. The scar tissue at the left ventricular free wall of the control hearts dilated during systole, whereas scar tissue containing transplanted cells was immobile. Although the surface area of transplanted scar tissue (22.9±6.2 mm2) was similar to that of control scar tissue (23.8±6.5 $mm^2$), scar thickness (1.9±0.9 mm, N=12) in hearts containing transplanted cells was twice ($p<0.01$) that of the control hearts (1.0±0.4 mm, N=10). Consistent with the above findings, the left ventricular volume of the transplanted hearts was 275±48 $mm^3$ (N=12) which was less ($p<0.01$) than the 360±94 $mm^3$ volume of the control hearts (N=10).

Although a detailed observation was not made of transplanted endothelial cells, staining with antibody against factor VIII revealed that more cells stained positively in scar tissue transplanted with endothelial cells than in the control scar tissue.

9. Angiogenesis in Myocardial Scar Tissue after Cell Transplantation: At 4 to 6 weeks after transplantation, examination by histology and electron microscopy showed that angiogenesis occurred in the transplanted fetal ventricular cardiomyocyte transplant. Significantly more arterioles and venules were found ($p<0.01$) in the cardiomyocyte grafts (1.2±0.6 vessels/0.8 $mm^2$, N=14) than in the control myocardial scar tissue (0.1±0.1 vessels/0.8 $mm^2$, N=14).

Similarly, angiogenesis occurred in the atrial cell, endothelial cell, smooth muscle cell and fibroblast cell transplants.

10. Transplanted Cells Limited Scar Expansion: At 4 to 6 weeks after transplantation of the cells, the heart rate and coronary flow did not differ among the sham, control and transplanted animals. The control myocardial wall at the site of injury had thinned and consisted of fibrous tissue and a few blood vessels. No cardiac muscle or lymphocytes were present. The control and transplanted hearts were larger ($p<0.01$) than the sham (undamaged) hearts. At 4 weeks after cryo-injury, 36.4±4.4% (mean±1 SE, N=5) of the left ventricular free wall in the pretransplant animals was replaced with a transmural scar. At 8 weeks, the scar tissue expanded ($p<0.01$) in the control group to 54.6±2.9% (N=5) of the free wall for the fetal cardiomyocytes. The scar tissue in the transplanted animals was 43.4±1.8% (N=5) of the left ventricular free wall. This did not significantly differ from the pretransplanted animals at 4 weeks after cryo-injury and was less ($p<0.05$) than the control hearts at 8-weeks after cryo-injury. The transplanted cardiomyocytes formed cardiac tissue which occupied 36.5±3.5% (N=5) of the scar tissue. The transplanted tissue visibly contracted. We were unsuccessful in measuring its contractility because of the contractions of the heart. After removing the hearts and separating the scar area, the transplanted region continued to contract when stimulated.

Similarly the atrial cell, smooth muscle cell, and fibroblast transplants limited scar expansion.

11. Improvement of Heart Function by Transplanted Cells: Ventricular function of hearts into which cells were transplanted immediately after myocardial injury was similar to that of control hearts. Analysis of covariance demonstrated no interaction between balloon volume and treatment group for developed pressures. Ventricular function of the transplanted and the control hearts when the cardiomyocytes were transplanted at 2 weeks after myocardial injury was different because an analysis of covariance demonstrated a significant (p<0.05) interaction between balloon volume and treatment group for developed pressures. The transplanted hearts had better (p<0.05) function than the control hearts. Similarly cells transplanted at 4 weeks after myocardial necrosis improved (p<0.05) myocardial function. The hearts transplanted at 2 weeks had higher (p<0.05, p<0.05, p<0.05) developed pressures at balloon volumes 0.1, 0.2, and 0.3 ml than hearts transplanted at 4 weeks.

In the measurements of ventricular function in the sham-operated, the transplanted and the control hearts, an analysis of covariance demonstrated a significant (p<0.05) interaction between balloon volume and treatment group for systolic, diastolic and developed pressures. Pairwise comparisons demonstrated a significant (p<0.05) depression in systolic and developed pressures in control animals compared to the sham-operated normal hearts. The transplanted hearts had better (p<0.05) function than the control hearts although both systolic pressure and developed pressure were lower (p<0.05) than the sham-operated normal hearts. Diastolic pressures were significantly lower in both the cryo-injured controls and the transplanted hearts than sham-operated normal hearts at higher balloon volumes due to the marked dilatation resulting from myocardial scar expansion.

12. Tissue Engineered Grafts: Cardiomyocytes, smooth muscle cells, fibroblasts, and endothelial cells were observed in the mesh of the grafts. The tissue that formed in the mesh stained strongly with haematoxylin and eosin.

SUMMARY

From the above results, it can be seen that we have successfully transplanted muscle and non-muscle cells in cardiac scar tissue. These cells formed viable tissue, altered structure of the scar, improved heart function, stimulated angiogenesis, and expressed a gene foreign to the scar. From these results, the following conclusions are drawn:

1. Cultured adult atrial cardiomyocytes could be successfully transplanted into the scar. The atrial tissue could be digested and the atrial cells immediately transplanted or the atrial tissue could be digested, cultured and passaged up to five times and then transplanted. Auto- and allo-transplantation of cultured adult atrial cardiomyocytes formed tissue within the scar. Heart function improved. Angiogenesis occurred. No immunorejection occurred with auto-transplantation of the adult atrial cardiomyocytes.

2. Smooth muscle cells can be successfully auto- or allo-transplanted into the scar. Smooth muscle tissue formed within the scar. No immunorejection occurred with the auto-transplantation. Angiogenesis occurred. Heart function improved. The cells can be freshly isolated, or cultured and passaged before transplanting.

3. Fibroblasts can be successfully transplanted into scar tissue. Scar thickness increased. Heart function improved. Angiogenesis occurred. Host cardiomyocytes survived in the scar. The cells can be freshly isolated, or cultured and passaged before transplanting.

4. The addition of cryo-precipitate to the injection site prevented leakage of the transplanted cells from the scar.

5. A plasmid containing a foreign gene to the scar tissue and heart tissue was transfected into the cultured cells to be transplanted. The cells were successfully transplanted into the scar tissue and expressed the foreign gene.

6. Cardiomyocytes, smooth muscle cells, skeletal muscle cells, fibroblasts, and endothelial cells can be successfully transplanted into fibrous membranes and non-degradable or biodegradable polymers to form tissue. The product of such a process would be a patch which can have various clinical and therapeutic uses. Such membranes may be made from Dacron or biodegradable sheets such as polyglycolic acid polymers with or without polylactic acid polymers. Such a patch can be associated with a pacemaker and be implanted close to a cardiac defect thereby providing a means of paced cardiomyoplasty.

7. Cell combinations could be successfully transplanted to form tissue within a scar to improve function, to stimulate angiogenesis and to form tissue.

8. The optimal time for transplantation is immediately after the acute inflammatory response to the myocardial injury has disappeared.

9. Adult mammalian atrial and ventricular cardiomyocytes can be successfully isolated from human myocardium, cultured, passaged and stored using the cell culture procedure described for human cardiomyocytes described in the Human Cell Isolation, Culturing and Storage section. Human cardiomyocytes can be prepared for long term storage in liquid nitrogen and thawed for culturing as described. Such cultured cells can then be used in forming grafts as discussed above.

10. The biological glue technique used in the cell transplantation procedure increased the number of cells transplanted in myocardial scar tissue. This invention enhanced the transplant success rate and maximized the improvement of heart function.

Co-transplantation of growth factors such as IGF-I, IGF-II, TGF-$\beta$1 and PDGF-B increases the survival of transplanted cells, induces transplanted muscle hypertrophy, and stimulates angiogenesis. Based on these findings, the use of other growth factors such as fibroblast growth factor and vascular endothelial growth factor are also possible. Such growth factors can be co-transplanted either alone or in combination. These techniques can increase transplanted muscle size and survival in myocardial scar tissue and damaged myocardial tissue.

11. Cultured cells can be employed to restore regional cardiac function and blood flow to regions in the heart damaged by acquired disease processes or absent because of congenital defects. During reconstructive surgery, the defective portion of the heart is removed and replaced with inert materials to secure a water-tight seal. Attaching a contracting tissue of myocytes to the reconstruction patch will permit the return of function to the destroyed region. Implantation of a collection of cells could restore function and improve the quality of life of the patients undergoing reconstructive surgery.

12. Most acquired or congenital cardiac defects are closed with inert materials intended to provide a water-tight seal. Instead of an inert material, a graft consisting of a biodegradable or non-biodegradable scaffolding supporting cultured cells can be employed to close such cardiac defects. The graft would employ myocytes enhanced with genes to increase perfusion and contractility (by increasing the size and number of myocytes). In addition, the endothelial cells can be applied to the blood surface of the graft to prevent intravascular clot formation in the heart. The endothelial cells could be genetically engineered so that they produce proteins that prevent clot formation on the blood surfaces. The cellular grafts will permit closure of acquired and congenital cardiac defects with functioning tissue which may improve heart function.

13. Cardiac surgeons frequently remove segments of the heart which have been damaged or are defective due to congenital abnormalities. A cellular graft permits an opportunity to restore function to regions which are usually closed with inert materials. The graft may consist of myocytes grown on biodegradable scaffolding. Endothelial cells can be grown on the blood interface layer. The cells will create a functioning graft which will replace the region removed at the time of surgery. The functioning myocardial graft could restore function for patients who have suffered a myocardial infarction and require removal of the destroyed regions. The functioning graft could re-establish systematic and/or pulmonary circulation for patients with extensive congenital defects undergoing reconstructive surgery. A functioning myocardial graft offers the promise of restoring an improved quality of life to disabled individuals.

EFFECT OF DONOR AGE ON CONTRACTILITY OF TRANSPLANTED RAT CARDIOMYOCYTES

The inability of heart muscle to regenerate following myocardial necrosis is an important clinical problem. Our previous research has shown survival and contractility of transplanted fetal rat cardiomyocytes (CMs) in adult rat skeletal muscle. The present study focuses on the effect of donor age on contractility of transplanted CMs.

Methods:

CMs were isolated from 18-day gestation, 5-, 22-, 32-, and 62-day old Sprague-Dawley rat hearts and cultured for 1 day. 2 to $5\times10^6$ cells in saline were injected into the skeletal muscle of one adult rat leg. The other leg (control) was injected with saline alone. Cell viability and function were assessed visually and by ultrasound and electrocardiography (ECG).

Results:

In the groups with transplanted fetal (n=12) and neonatal (n=4) CMs, rhythmic contractions (73±12 beats/min (n=1 1) and 43±21 beats/min (n=3)) were found only in the transplanted area. These contractions were not observed in the control legs. Contractions were not observed at sites transplanted with CMs from 22-, 32-, and 62-day donor animals (n=4 for all groups).

Conclusion:

Donor age is important for maintaining contractility of CMs after transplantation into skeletal muscle.

INDUCTION OF ANGIOGENESIS BY ENDOTHELIAL CELLS TRANSPLANTED INTO MYOCARDIAL TRANSMURAL SCARS DID NOT IMPROVE CARDIAC FUNCTION IN INFARCTED HEARTS

We speculated that artificial induction of angiogenesis might improve perfusion, alleviate angina and restore cardiac function in cases where revascularization does not occur spontaneously after myocardial infarction (e.g., in scar tissue). The present study evaluated whether allogenic and syngenic endothelial cells transplanted into myocardial scar tissue induce new blood vessel formation and whether angiogenesis (if any) induced by transplanted cells affects the function of the scarred heart. The effect of transplanted cells upon blood vessel formation in myocardial scar tissue has not been studied previously.

Methods and Results: Transmural scars were produced at the left ventricular free wall of adult rats hearts by cryo-injury. Two weeks later, cultured adult rat aortic endothelial cells (transplanted group) or culture media (control group) were injected into the myocardial scars of rats immunosuppressed with cyclosporin A (25 mg/kg/day). Transplanted cells were observed at transplanted sites at day 1 and 7, but not at day 14 (n=2). At 6 weeks after transplantation, the number of capillaries in the scars of the transplanted group (3.4±2.0, n=10) was greater (p<0.01) than that in the control group (1.0±0.6, n=9). Blood flow measured by radioactive $^{57}$Co labeled microspheres was greater (p<0.01) in the transplanted group (6.85±2.27%, n=9) than in the control group (3.78±0.99%, n=8). There was no difference in scar size and heart function between two groups measured by planimetry and Langendorf preparation.

Conclusion: Angiogenesis was induced in the scar tissue by endothelial cell transplantation. Since no myocytes were present in the scar, function did not improve. Endothelial cell transplantation in patients with incomplete infarction may restore perfusion, relieve angina and restore function.

Methods

Experimental Animals: All procedures performed on animals were approved by the Animal Care Committee of The Toronto Hospital. Experiments were performed according to the "Guide to the Care and Use of Experimental Animals" published by the National Institutes of Health (NIH publication 85-23, revised 1985). Sprague-Dawley rats (Charles River Canada Inc, Quebec, Canada) were used for allogenic transplantation. Male rats, weighing 330 to 360 g, were used as recipients and donors of endothelial cells. Sygenic Lewis rats (Male, 250–300 g, Charles River Canada Inc, Quebec, Canada) were used for autologus transplantation.

Cell Isolation and Culture: Endothelial cells from rat aorta were isolated and cultured as previously described (Mickle et al., *J. Mol. Cell. Cardiol.* 22:1297–1304, 1990). In brief, descending thoracic aortic segments were obtained from rats under general anesthesia as described in the next section. The blood vessels were washed with phosphate buffered saline solution (PBS; composition in mmol/L: NaCl 136.9, KCl 2.7, $Na_2HPO_4$ 8.1, KH2PO4 1.5, pH 7.3) and connective tissue was removed. The aortic segment was then flushed with enzyme solution (0.1% collagenase and 0.2% trypsin in PBS) and incubated with the enzyme solution for 30 minutes at 37° C. After incubation, endothelial cells were isolated by flushing the inside of aortic segments with culture medium (Medium 199 containing 20% fetal bovine serum, 100 U/ml of penicillin, 100 ug/ml of streptomycin, and 0.5% heparin salt) three to five times. The isolated cells were cultured at 37° C. in 5% $CO_2$ and 95% air in culture medium.

Cell Identification: The purity of endothelial cell cultures was confirmed by a immunohistochemical stain using antibody against factor VIII-related antigen as previously described (Mickle et al., *J. Mol. Cell. Cardiol.* 22:1297–1304, 1990). In brief, the cultured endothelial cells were fixed in methanol for 15 minutes at −20° C. After washing three times with PBS, the cells were incubated with rabbit immunoglobulin G against factor VIII-related antigen (Dimension Laboratory, Inc) at 37° C. for 45 minutes. After incubation, the cells were washed three times (15 minutes per wash) with PBS, then incubated with goat anti-rabbit immunoglobulin G conjugated with peroxidase at 37° C. for 45 minutes, washed three times (15 minutes per wash) with PBS, and immersed in diaminobenzidine-$H_2O_2$ (2 mg/ml diaminobenzidine, 0.03% $H_2O_2$ in 0.02ml/l phosphate buffer) solution for 15 minutes. After a final wash in PBS, the samples were photographed.

Quantitation of VEGF Protein Levels in Cultured Endothelial Cells and Secreted by Cultured Cells: Purified endothelial cells were cultured in cell culture medium for 3 days. The supernatants (n=5) were collected, centrifuged at 14,000 g for 10 min. to remove cell debris, and were saved for protein quantitation. The cultured cells (n=5) were washed 3 times with PBS and collected by scraping with cell scraper. After centrifugation at 580 g for 3 min., the cell pellets were resuspended in 1 ml of PBS and sonicated for 1 min. The samples were centrifuged at 14,000 g for 10 min. The supernatants were collected for protein quantitation. The protein concentration was measured using the Bio-Rad protein assay (Bio-Rad, Richmond, Calif.). VEGF protein levels in culture medium and endothelial cells were quantitated by chemiluminescent slot blot analysis. Culture medium incubated without cells was used as a control. Forty micrograms of protein from culture medium or from cultured endothelial cells were loaded onto a 0.2 μm nitrocellulose membrane (Schleicher & Schuell Inc., Keene, N.H.) using the Minifold II Slot Blotting System (Schleicher & Schuell Inc., Keene, N.H.). Standards of VEGF (2, 5, 10, 25 ng) (Sigma, Mississauga, ONT) were loaded on the same membrane. After drying at room temperature for 10 minutes, the membrane was washed twice in TTBS buffer (50 mM Tris-HCl buffer pH 7.4 and 0.1% of Tween-20) for 5 minutes. Subsequently, the membrane was treated for 60 minutes with blocking buffer (Boehringer Mannhein, GmbH, German). Monoclonal antibodies against VEGF (Sigma, Mississauga, ONT) (1:3000, diluted with 0.5×block buffer) were added and incubated overnight at 4° C. After washing twice with TTBS for 5 minutes each, the membrane was incubated with goat anti-mouse-HRP conjugated antibody (1:3000 dilution)(Bio-Rad Laboratories, Hercules, Calif.) for 60 minutes at room temperature. The membrane was again washed twice with TTBS for 10 minutes twice. VEGF proteins were detected by chemiluminescence using the Boehringer Mannheim detection kit (Quebec, Canada). A densitometric analysis of the standard and sample bands was performed with a Bio-Rad image analysis system (Bio-Rad Lab. Hercules, Calif.). Standard curves of VEGF were generated and VEGF quantity in culture medium and cultured endothelial cells was calculated based on the standard curve. The results (mean±SD) are expressed as ng of VEGF/mg protein.

Preparation of Cells for Transplantation: Cultured endothelial cells were passaged twice before transplantation to increase the number of cells. Prior to transplantation, the cultured endothelial cells were detached from culture dish with 0.05% trypsin in PBS. After centrifugation in 580g for 3 minutes, the cell pellets were resuspended in culture medium at a concentration of $1.0 \times 10^6$ cells/10 ul. A 60 ul cell suspension was used for each transplantation.

Myocardial Scar Formation: Rats were anesthesized by intramuscular injection of ketamine hydrochloride (20 mg/kg body weight) followed by intraperitoneal injection of sodium pentobarbital (30 mg/kg body weight). The anesthesized rats were intubated and positive pressure ventilation was performed with room air supplemented with oxygen and isoflurane (0.2–1.0%) using a Harvard ventilator. The electrocardiogram was monitored during operation.

The heart was exposed through a 2- to 3-cm left lateral thoracotomy incision. Cryoinjury was produced in the left ventricular free wall (LVFW) with a metal probe (8×10 mm in diameter) cooled to −190° C. by immersion in liquid nitrogen. It was applied to the LVFW for one minute and this procedure was repeated ten times. The muscle and skin were closed with 3-0 silk sutures. Penlong XL (benzathine penicillin G 150,000 U/ml and procaine penicillin G 150,000 U/ml) was given intramuscularly (1 ml/kg) and buprenorphine hydrochloride (0.01 mg/kg) was administered after each operation. The cryoinjured rats were randomly divided into two groups: transplantation and control.

Endothelial Cell Transplantation: At two weeks after cryoinjury, cell transplantation was performed. Under general anesthesia, the heart was exposed through a midline sternotomy. Endothelial cell suspension (60 ul, $6 \times 10^6$ cells) was injected into the center of the scar tissue in the transplantation group using a tuberculin syringe, and same amount of culture media was injected into the scar in the control group. The chest was closed with 3-0 silk sutures. Antibiotics and analgesics were given as previously described. Cyclosporine A (25 mg/kg/day) was administered subcutaneously to both transplanted and control groups.

Identification of Transplanted Endothelial Cells: The transplanted cells were identified in two ways.

(1) At day 1, 7 and 14 post transplantation, two rats from transplanted and control groups were sacrificed by exanguination under general anesthesia. The hearts were fixed in with 10% phosphate-buffered formalin solution for 2 days and cut into 3-mm sections. The sections were fixed in 5% glacial acetic acid in methanol, embedded in paraffin, and cut to yield 10 μm which were stained with hematoxylin and eosin as described by the manufacturer (Sigma Diagnostics, St. Louis, Mo.).

(2) The transplanted cells also were identified by detection of green fluorescent protein expressed by the transplanted cells. At 2 days pre-transplantation, cultured endothelial cells were lipofectamine-transfected with a plasmid encoding green fluorescent protein. The transfected cells were cultured, harvested and transplanted as described previously. At end of the study, monoclonal antibodies against green fluorescent protein were used to localize the transplanted endothelial cells by avidin-biotin-peroxidase complex technique (Hsu, S. M. *Am. J Pathol.*, 75:816–821, 1981). Briefly, sections were incubated with a solution of 3% $H_2O_2$ in 70% methanol for 30 minutes to inhibit endogenous myocardial peroxidase. Nonspecific protein binding was blocked with 2% normal goat serum in 0.05 M Tris buffer (pH 7.4) for 15 minutes, primary antibodies against green fluorescent protein (Cedarlane Lab., Hornby, Ontario) were added and the samples were incubated at 37° C. for 30 minutes followed by an overnight incubation at 4° C. Negative control samples were incubated in PBS (without the primary antibodies) under the same conditions. After washing with PBS (three times for 5 minutes each), a biotin-labeled secondary antibody (1:250, Vector Lab. Inc. Burilingame, Calif.) was added and the specimens were incubated at room temperature for 1 hour. The samples were rinsed 3 times for 5 minutes each in fresh PBS and reacted with an avidin-biotin complex conjugated with peroxidase at room temperature for 45 minutes. Visualization was performed with a diaminobenzidine solution (0.25 mg/ml in 0.05 Tris-HCl buffer containing 0.02% $H_2O_2$) for 10 minutes. The samples were then covered with crystal mounts and photographed.

Blood Flow Measurement with Radionuclide-labeled Microspheres: At six weeks after transplantation, blood flow to the normal and scar tissue in the transplanted (n=9) and control groups (n=8) was measured using radionuclide-labeled microspheres (Pang, C. Y. *Plastic and Reconstructive Surgery* 74(4):513–521, 1984). Rats were anesthesized and heparin sodium (200 units) was then administered intravenously. Hearts were excised and perfused in a Langendorf apparatus with 0.9% saline solution to wash out all blood cell remnants in the coronary vascular bed. Ten ml of 20 mEq KCl solution was injected through the coronary arteries to arrest the heart completely, and the heart was perfused with 0.9% saline solution for 10 minutes.

$^{57}$Co-labeled microspheres (5 uCi, New England Nuclear, Boston, Mass.) were suspended in 2 ml of 0.9% saline containing 5% sucrose and 0.05% Tween 80. The suspension was vortexed vigorously for 2 minutes immediately before injection. The microspheres were infused over a 5 second period through a needle connected to the ascending aortic root.

Ventricles were dissected into normal tissue, scar tissue, and tissue in the borderline area. Each section was weighed and the radioactivity was then determined using a gamma counter at the window setting of 110 to 138 KeV. The data was expressed as counts per minute (cpm)/mg of tissue. The ratio of cpm/mg in scar and borderline tissue to normal tissue was calculated, expressed as the percentage, and compared between transplanted and control hearts.

Heart Function Measurement: Six weeks after transplantation, heart function in transplanted (n=10) and control (n=9) groups was measured using a Langendorf preparation (Stephen, S. E. *Annals of Thoracic Surgery* 59:1127–1133, 1995). Rats were anesthesized and heparin sodium (200 units) was administered intravenously. Hearts were quickly isolated and perfused at 37° C. in a Langendorf apparatus with filtered Krebs-Hanseleit buffer (mmol/L: NaCl 118, KCl 4.7, $KH_2PO_4$ 1.2, $CaCl_2$ 2.5, $MgSO_4$ 1.2, $NaHCO_3$ 25, glucose 11, pH 7.4) equilibrated with 5% carbon dioxide and 95% oxygen at a pressure of 100 cm $H_2O$. A latex balloon was inserted into the left ventricle through the mitral valve and connected to a pressure transducer (Model p10EZ; Viggo-Spectramed, Oxnard Calif.) and a transducer amplifier and differentiator amplifier (Model 11-G4113-01; Gould Instrument System Inc, Valley View Ohio).

After 20 minutes of stabilization, the coronary flow was measured by the timed collection in the empty beating state. The balloon size was increased in 0.02 ml increments from 0.04 to 0.6 ml by the addition of saline solution. The systolic and end-diastolic pressure and maximal and minimal dp/dt were recorded at each balloon volume. The developed pressure was calculated as the difference between the systolic and end-diastolic pressure.

Measurement of Left Ventricular Remodeling: The epicardial and endocardial surfaces of the normal and scar tissue in the LVFW were measured by the technique of Pfeffer (Pfeffer Am J Physiol 1991;260:H1406-14) and Jugdutt and Khan Circulation 1994;89:2297–307). Briefly, the hearts were fixed in distension (30 mmHg) with 10% phosphate-buffered formalin solution for 2 days. The atria were excised, the ventricular weight and the size of the scar on epicardial surface were measured, and ventricular volume was measured by water displacement. After that, the hearts were cut into sections of 3 mm thickness. For each section, the area of normal and scar tissue in the LVFW were traced onto a transparency and quantified using computed planimetry (Jandal Scientific Sigma-Scan, Corte Madera, Calif.). The lengths of LVFW and scar tissue on both the endocardial and epicardial surfaces of each section were measured. The surface areas of the endocardial and epicardial scar tissue and the LVFW were measured as the sum of the endocardial length and epicardial length times the section thickness (3 mm). The surface area percentage of scar tissue in the LVFW was calculated as follows: (endocardial scar size+epicardial scar size)/(endocardial LVFW+ epicardial LVFW)×100.

Measurement of Capillaries in Scar Tissue: The heart sections were used for immunohistochemical staining of endothelial cells. The sections were incubated with xylene twice for 5 minutes each, 100% ethanol twice for 2 minutes each, and then with 70% ethanol twice for 1 minute each. The sections were incubated with rabbit immunoglobulin G against factor VIII-related antigen and endothelial cells were identified as described in the Cell Identification section above. The stained vasculoendothelial cells in the transplanted and control groups were counted using a light microscope at 400× magnification. The result was expressed as the number of capillary vessels/field.

Syngeneic endothelial cell transplantation: To evaluate angiogenesis induced by transplanted endothelial cells in the absence of an inflammatory reaction, endothelial cells isolated from adult Lewis rat aorta were transfected and transplanted into myocardial scar tissue of syngeneic rat hearts (n=5) two weeks after the scarring procedure. The transplanted cells were identified in the scar tissue at 6 weeks after transplantation by immunohistochemical staining. The number of capillaries in the scar areas of transplanted and control hearts was counted and compared. All the procedures performed on these animals were same as described above, except that cyclosporine was not administered after cell transplantation.

Statistical Analysis: Data were expressed as the mean±standard error. Statistical Analysis System software was used for all analysis (SAS Institute, Cary, N.C.). Student's t-test was used for comparison of the results. Cardiac function data were evaluated for the transplantation and control groups using intracavitary volume as the variant factor and systolic, end-diastolic, and developed pressure as dependent variables.

Results

Cultured endothelial cells were distinguished from fibroblasts and vascular smooth muscle cells by morphologic criteria and growth characteristics. The endothelial cells were oval shaped, in contrast to the spindle-shape of cultured fibroblasts and vascular smooth muscle cells. Cultured endothelial cells grew in a "cobblestone" pattern whereas fibroblasts grew in a "whirling" pattern and vascular smooth muscle cells grew in a "hill and valley" pattern. In addition, cultured endothelial cells stained positively for factor VIII-related antigen. The purity of the culture to be transplanted was more than 95%.

We found that cultured vascular endothelial cells contained VEGF (0.007 and 0.005 ng/$\mu$g of cell protein, N=2). The VEGF molecules in the cultured cells were secreted into cultured medium: VEGF protein levels (0.331 and 0.229 ng/50 $\mu$l, N=2) in conditioned medium (i.e., in which cells were cultured) was greater than in medium not exposed to endothelial cells (0.143 ng/50 $\mu$l, N=1).

At one day after transplantation, two rats in the transplanted group were sacrificed in order to identify transplanted cells. A large endothelial cell cluster was observed within each scar. There was no increased capillary network around the cell clusters compared with control rats.

At one week after transplantation, there were some capillaries around the transplanted endothelial cell cluster within each scar. The size of the endothelial cell cluster was, however, much smaller than that observed one day after transplantation.

At two weeks after transplantation, there were more capillaries within the scar but the endothelial cell cluster was no longer present.

Figure 2:
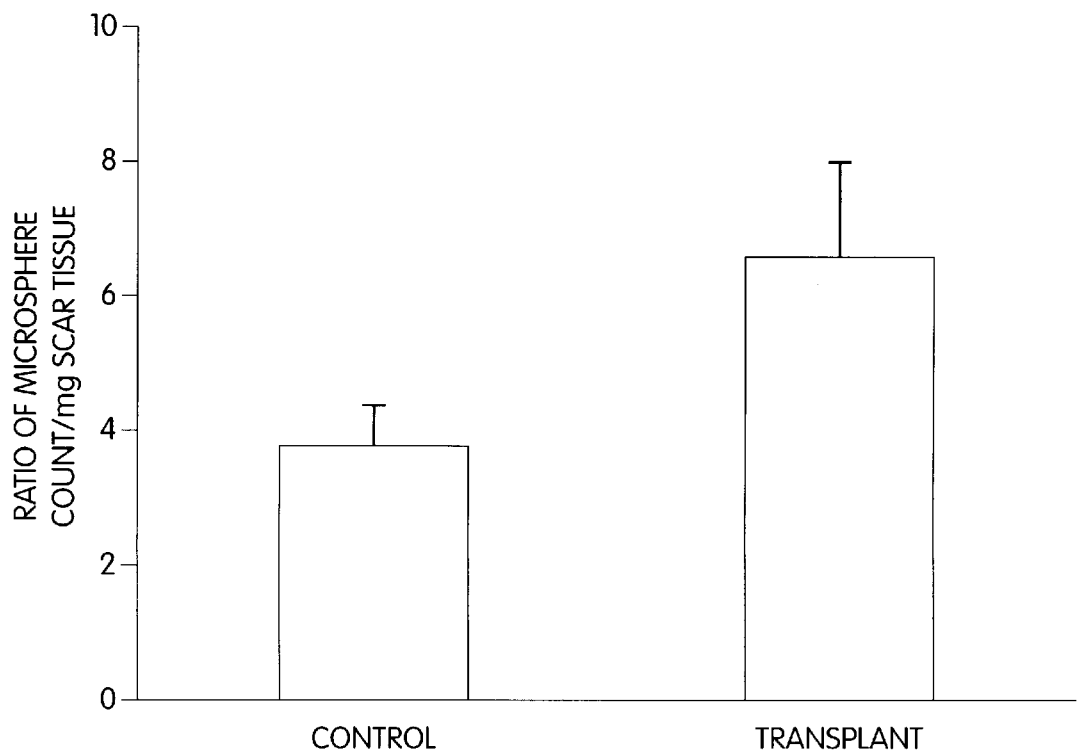
FIG. 2 is a graph showing the amount of blood flow (represented as microsphere count) to control scar tissue and scar tissue transplanted with endothelial cells.

Six weeks after transplantation, the number of blood vessels in the scar tissue of the transplanted group (3.4±2.0 vessels/0.8 $mm^2$, n=10) was significantly greater (p<0.01) than within control (non-transplanted) scars (1.0±0.6, n=9). Most of blood vessels are capillaries without smooth muscle components. In agreement with the number of blood vessels, the blood perfusion (represented as microsphere count) in the scar tissue of transplanted hearts (6.85±2.27% of normal myocardium) was greater (p<0.01) than that of control hearts (3.78±0.99%) (FIG. 2).

In syngeneic cell transplantation the transplanted cells also induced angiogenesis in the myocardial scar tissue. The density of capillaries in the scar tissue of the transplanted group was 2.6±1.5 vessels/0.8 mm$^2$, which was significantly (p<0.01) greater than that in the control group (1.1±0.6). Transplanted endothelial cells were incorporated into capillaries at the transplant site.

In morphological studies of the hearts, there was no difference in weights of heart, left ventricle, scar tissue, and animal body between transplanted and control groups (Table 1). Ventricular volume in transplanted hearts was similar to that of control hearts. The size of the scar tissue in transplanted group was also not different from that of control group.

Figure 3:
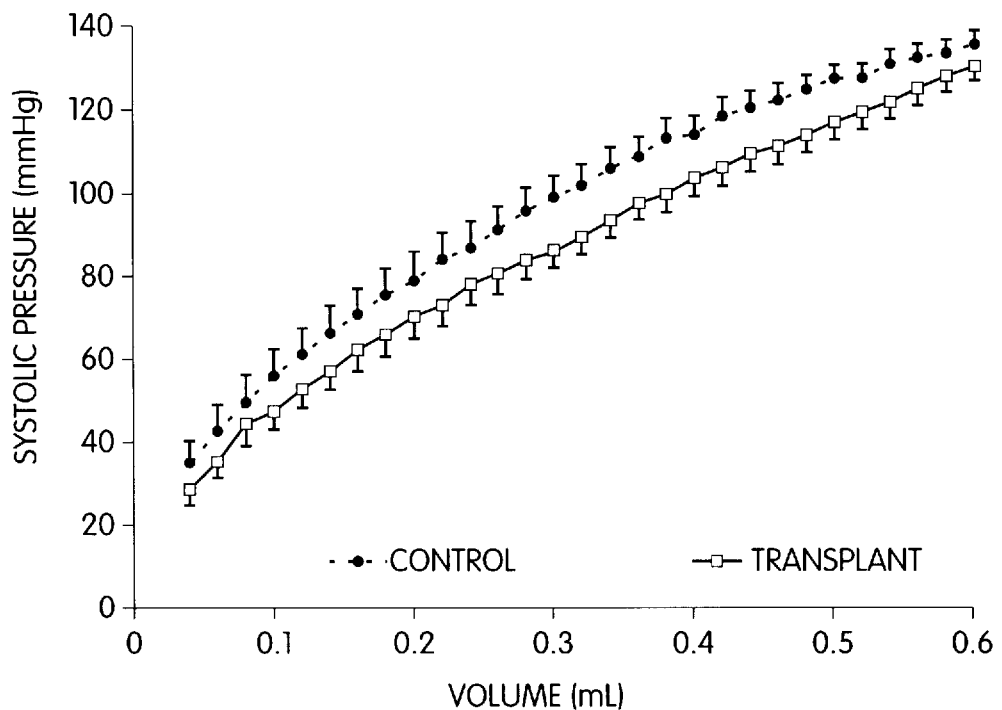
FIG. 3 is a graph showing systolic pressure of transplantation and control hearts with increasing balloon volume.
Figure 4:
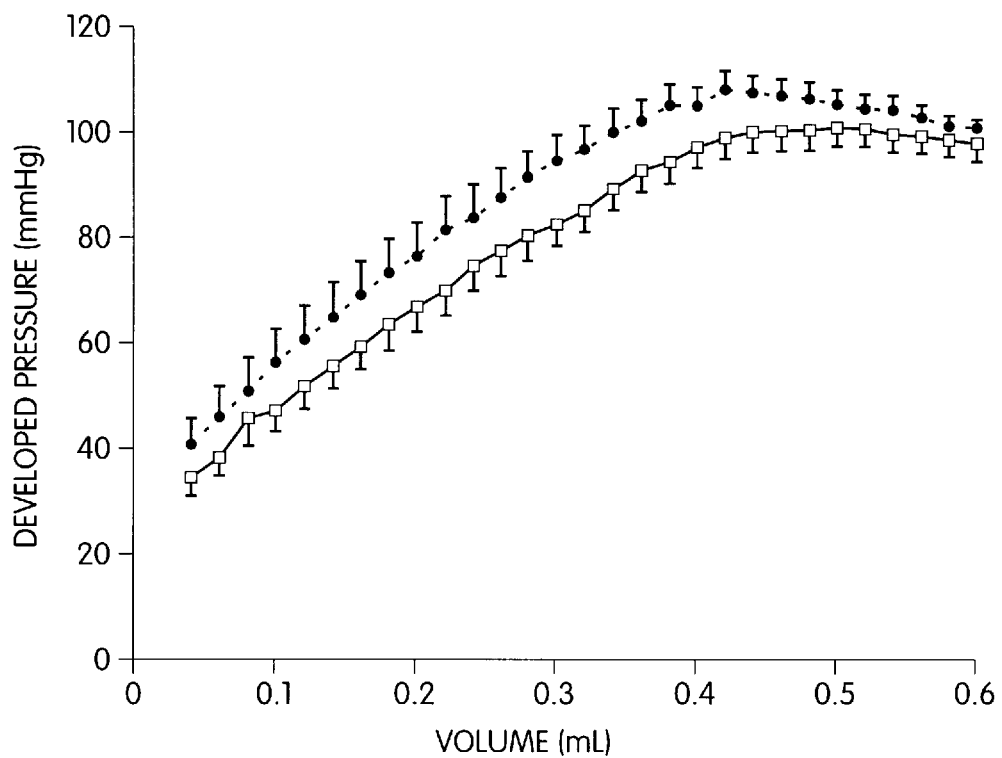
FIG. 4 is a graph showing developed pressure of transplantation and control hearts with increasing balloon volume.

There were no statistically significant differences in systolic and developed pressures between transplanted and control hearts (FIGS. 3 and 4), and no differences in coronary flow and heart rate (Table 1).

helial cell transplantation has shown that angiogenesis occurrs without inflammatory reaction, factors released by inflamatory cells might play a role in blood vessel formation induced by allogenic endothelial cell transplantation. Capillary density in scar tissue subjected to allogenic cell transplantation was 1.3 time greater than that subjected to syngeneic cell transplantation. This difference in capillary density may be due to lymphocyte infiltration.

Although blood flow was increased by endothelial cell transplantation in our experimental model, increased blood flow did not have any effects on left ventricular remodeling and function. We found muscle cells in the scar tissue of a few hearts but the number of the muscle cells may not be sufficient to improve heart function. There were no differences in heart volume, heart weight, and scar size between transplanted and control hearts. In the analysis of function, there were no differences in heart rate, coronary flow, systolic and developed pressures between two groups.

We observed that the 2 week old scar was less mature and contained more blood vessels and fibroblasts than 4 week

TABLE 1

Hemodynamics and heart dimensions in transplantation and control groups[a,b]

| Group | Coronary flow (ml/min) | Heart rate (bpm) | Ventricular weight (g) | Ventricular volume (ml) | Scar size (mm$^2$) |
|---|---|---|---|---|---|
| Transplant | 20.9 +/− 4.36 | 279 +/− 15 | 1160 +/− 168 | 1.86 +/− 0.27 | 109 +/− 19 |
| Control | 21.9 +/− 3.82 | 289 +/− 19 | 1150 +/− 137 | 1.79 +/− 0.21 | 110 +/− 19 |

[a]Data are shown as the mean +/− standard error
[b]There were no significant differences in all parameters between two groups.

The transplanted endothelial cells stimulate angiogenesis, demonstrated by an increase in the number of capillaries in the scar tissue and increased blood perfusion in scar tissue as illustrated by microsphere perfusion studies. However, the induced angiogenesis in transmural scar tissue did not improve infarcted heart function.

There are three possible mechanisms of increased angiogenesis by endothelial transplantation: (1) formation of blood vessels by transplanted endothelial cells; (2) angiogenesis stimulated by growth factors secreted by transplanted endothelial cells; (3) angiogenesis stimulated by an inflammatory reaction induced by transplanted endothelial cells.

Endothelial cells are the most important component for blood vessel formation. Our in vivo study showed that transplanted endothelial cells become part of newly formed capillaries in syngeneic cell transplantation. These data suggested that transplanted endothelial cells are involved in blood vessel formation. However, the data obtained from allogeneic endothelial cell transplantation suggested that newly formed capillaries in the scar tissue were grown from recipient heart endothelial cells. We found transplanted cells at 1 and 7 days after transplantation, but did not observe transplanted cells after 14 days post transplantation. Additional evidence of this conclusion is that there was no immunologic reaction around capillary vessels in the scar. If the transplanted allogenic endothelial cells become part of the newly formed capillaries, lymphocyte infiltration should be observed around the blood vessel. These data illustrate that transplanted endothelial cells are involved in new blood vessel formation and also stimulate angiogenesis. In the latter situation, angiogeneic factors secreted by transplanted cells may play an important role in this process.

Angiogenesis in our animal model might also be stimulated by inflammatory reactions. Although syngeneic endotold scar, which was firm connective tissue. In addition, we found that cardiomyocyte transplantation was most successful after the inflammatory reaction resolved and before significant scar expansion and ventricular dilatation occurred.

The finding of increased angiogeneis in transmural scars induced by endothelial cell transplantation gives rise to a new technique for induction of angiogenesis. We observed an increased number of capillary vessels within the scars of rat hearts that were transplanted with endothelial cells. In contrast, we observed an increased number of arterioles and venules in scars transplanted with fetal cardiomyocytes. If endothelial cells and cardiomyocytes are co-transplanted into myocardial scars and endothelial cells augment the blood flow into the transplanted area, the survival and function of transplanted cardiomyocytes might be enhanced. It would be possible to obtain ventricular cardiomyocytes from transvenous endomyocardial biopsy and endothelial cells from saphenous vein or omental fat and culture those cells for subsequent auto co-transplantation.

In addition to morphologic evidence of increased angiogenesis, we demonstrated that blood flow to scar tissue was increased. Because there was usually adhesion between the scar area and the chest wall from the previous two operations (scarring and transplantation), blood flow to the scar area may result from two sources, one from coronary arteries and the other from the chest wall by non-coronary collateral vessels produced by adhesion. If blood flow from chest wall adhesion is counted together with blood flow from coronary artery, it obscures the effect of angiogenesis per se on blood flow to the scar area. Therefore, we injected microspheres into isolated heart preparations, although for actual blood flow estimation, injection of microspheres into left atrium or left ventricle in vivo may be more physiologic. Because there were areas of non-transmural infarction in the periphery of the cryoinjured lesions, the left ventricular free wall was divided into three parts: normal area, transmural infarct area, and borderline area. The blood flow to the borderline areas was always between that of the normal and complete transmural infarct area.

OPTIMAL TIME FOR CARDIOMYOCYTE TRANSPLANTATION FOR MAXIMIZING MYOCARDIAL FUNCTION AFTER LEFT VENTRICULAR NECROSIS

After myocardial infarction, damaged myocardium undergoes both acute and chronic inflammatory reactions. During this process the necrosed cardiac cells are replaced with fibrotic tissue and ventricular remodeling progresses. Ventricular pressure stretches and thins the healing area and ventricular dilatation occurs. A ventricular aneurysm may form and congestive heart failure may result. Limitation of post infarction ventricular remodelling is important to prevent expansion and thinning of the infarct region and thinning, and progressive ventricular dilatation, which results in congestive heart failure. The addition of cardiac tissue to replace the scar tissue may prevent infarct thinning and preserve chamber size and ventricular function. We had shown that fetal cardiomyocytes transplanted into a LVFW scar formed cardiac tissue and improved myocardial function. Transplantation was arbitrarily performed at 4 weeks after cryo-necrosis of the LVFW when ventricular dilatation was already present. However, the optimal time for cardiomyocyte transplantation to provide the best ventricular function is important. The acute inflammatory reaction could destroy the transplanted cardiomyocytes that are introduced too soon after myocardial infarction. On the other hand, cardiomyocyte transplantation after significant scar expansion may be of limited benefit. Therefore, the present study investigated the optimal time for cell transplantation after myocardial injury.

Summary

Methods:

(1) Scar expansion studies: The rats were sacrificed at 0, 1, 2, 4, and 8 weeks after cryo-injury and the scar area was measured by planimetry (N=7 each).

(2) Transplantation studies: Fetal rat cardiomyocytes (transplant) or culture medium (control) were transplanted immediately (N=8 each), 2 weeks (N=8 each) and 4 weeks (N=12 each) after cryo-injury. At 8 weeks after cryo-injury, rat heart function was evaluated using a Langendorff preparation. Scar and transplanted cardiomyocytes were assessed histologically.

Results:

(1) A transmural injury occurred immediately after cryo-injury. An inflammatory reaction was more evident at 1 week than 2 weeks. Although the scar size did not significantly change between week 1 and 2, it expanded (p<0.01) at 4 and 8 weeks.

(2) At 8 weeks after myocardial injury, cardiomyocytes transplanted immediately after myocardial injury were not found in the myocardial scar tissue. Scar size and myocardial function were similar to those of the control hearts. Cardiomyocytes transplanted at 2 and 4 weeks formed cardiac tissue, which occupied 34% and 31% of total scar area, respectively, and limited (p<0.01) scar expansion compared to control hearts. Both transplant groups had better (p<0.001, <0.001) heart function than the control groups. Developed pressure was greater (p<0.01) in the hearts transplanted cells at 2 weeks than at 4 weeks.

Conclusion:

Cardiomyocyte transplantation was most successful after the inflammatory reaction resolved and before significant scar expansion and ventricular dilatation occurred.

Material and Methods

Experimental animals: All procedures performed on animals were approved by the Animal Care Committee of The Toronto Hospital. Experimental animals used were male Sprague-Dawley rats (Lewis, Charles River Canada Inc. Quebec, Canada), weighing 450 grams. Cardiomyocytes obtained from 18-day gestational rat hearts were cultured prior to transplantation. All experiments were performed according to "A Guide to the Care and Use of Experimental Animals" of the Canadian Council on Animal Care and the "Guide for the Care and Use of Laboratory Animals" NIH publication 85-23, revised 1985).

Myocardial scar generation and evaluation: Myocardial scar tissue was generated as described in Example I above. Briefly, rats were anesthetized with ketamine (22 mg/kg body weight, intramuscular) followed by an intraperitoneal injection of pentobarbital (30 mg/kg body weight). The anesthetized rats were intubated and positive pressure ventilation was maintained with room air supplemented with oxygen (6 L/minute) using a Harvard ventilator (Model 683, South Natick, Mass., USA). The rat heart was exposed through a two cm left lateral thoracotomy. Cryo-injury was produced at the left ventricular free wall (LVFW) with a liquid nitrogen probe. The muscle layer and skin were closed with 5-0 vicryl sutures. The rats were monitored for 4 hours postoperatively. Penlog XL (benzathine penicillin G 150,000 U/ml and procaine penicillin G 150,000 U/ml) were given intramuscularly (0.25 ml/rat) every three days for 1 week after surgery and buprenorphine (0.01–0.05 mg/kg body weight) was administrated subcutaneously every 8 to 12 hours for the first 48 hours following surgery.

Figure 5A:
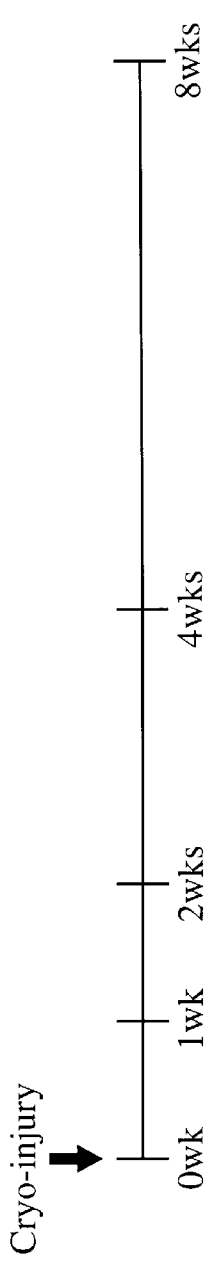
FIGS. 5A–B are diagrams showing the design of cardiac cryo-injury/endothelial cell transplantation experiments. Rats were sacrificed at 1, 2, 4 and 8 weeks (wks) after cryo-injury of the left ventricular free wall (LVFW) for the histological study of the remodeling of the left ventricle. After cryo-injury of the LVFW the animals were randomly divided into three groups (group 1, 2 and 3). In each group, half of animals were transplanted with cardiomyocytes (transplant) and half animals were transplanted with cultured medium (control). Transplantation into the center of the LVFW scar was performed immediately (group 1), 2 weeks (group 2) and 4 weeks (group 3) after myocardial injury. All the animals were sacrificed at 8 weeks after cryo-injury for histological and functional studies.
Figure 5B:
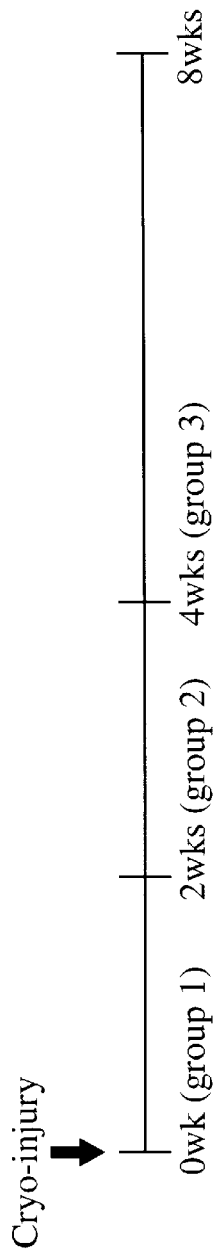

The LVFWs of 35 animals were cryo-injured. Immediately after cryo-injury and at 1, 2, 4, and 8 weeks after injury, 7 animals chosen at random were sacrificed under general anesthesia (see FIG. 5 for a schematic diagram of the experimental design). The hearts were then fixed in distension (30 mm Hg) with 10% phosphate-buffered formalin solution for 24–48 hours and then cut into 3 mm thick sections. All sections were used for assessment of myocardial and scar sizes. For each section, the area of scar tissue in the LVFW was traced onto a transparency and quantified using computerized planimetry (Jandal Scientific Sigma Scan, Fairfield, Conn., USA). Scar length was calculated as the average of endocardial scar length and epicardial scar length. Scar area was calculated as the scar length×section thickness (3 mm). The total scar area in size was calculated as the sum of the scar areas for all of the tissue sections showing scars. The LVFW myocardial size was calculated using the same equation. The percentage of the LVFW occupied by the scar was calculated as scar size/LVFW size×100.

Histological studies: The fixed heart sections were embedded in paraffin and cut to yield 10 μm thick sections. The sections were stained with haematoxylin and eosin as described by the manufacturer (Sigma Diagnostics, St. Louis, Mo.).

Cell culture and preparation for transplantation: Cardiomyocytes from fetal rat hearts were isolated, purified and cultured as previously described (Li, R-K, et al. *J. Tissue Culture Methods* 14:93–100, 1992). Briefly, the cells were cultured for 24 hours in Iscove's modified Dulbecco's medium containing 10% fetal bovine serum, 100 U/ml penicillin and 100 ug/ml streptomycin at 37EC, 5% $CO_2$ and 95% air. The cultured cardiomyocytes were detached from the cell culture dish with 0.05% trypsin in phosphate-buffered saline (PBS). After centrifugation at 580×g for 3 minutes, the cell pellet was resuspended in culture medium at a concentration of $16 \times 10^6$ cells/ml. A 0.25 ml cell suspension was used for each transplantation.

Cardiomyocyte transplantation: The LVFW of 56 adult rat hearts were cryo-injured as described above. The animals were randomly divided into 3 groups (see FIG. 5, bottom). In group one, 8 animals were transplanted with cultured cardiomyocytes (transplant) and 8 animals were transplanted with culture medium (control) immediately after myocardial injury. In group two, animals were transplanted with cells and culture medium (N=8 each) 2 weeks after myocardial injury. In group three, control and transplanted animals (N=12 each) were transplanted 4 weeks after myocardial injury. All animals were maintained 8 weeks after the transplant procedure.

Under general anesthesia, the hearts were exposed through a midline sternotomy. A fetal rat cardiomyocyte suspension (0.25 ml, $4 \times 10^6$ cells) or culture medium (0.25 ml) was injected once into the center of the scar tissue of the transplanted and control animals, respectively, using a tuberculin syringe. The chest was closed with 5-0 vicryl sutures. Antibiotics and analgesics were given as described in the "Myocardial Scar Generation and Evaluation" section below. Cyclosporin A, at a dose of 5 mg/kg body weight/day, was administered subcutaneously to the control and transplanted rats. The rats were housed in cages with filter tops.

Myocardial function studies: At 8 weeks after myocardial injury, the heart function of control and transplanted animals transplanted at 0, 2, and 4 weeks after myocardial injury was measured using a Langendorff preparation (Stephen, S. E. Annals of Thoracic Surgery 59:1127–1133, 1995). The rats were anesthetized and heparin (200 units) was administered intravenously. The hearts were quickly isolated from rats and perfused in a Langendorff apparatus with filtered Krebs Heinseleit buffer (mmol/L NaCl 118, KCl 4.7,$KH_2PO_4$ 1.2, $CaCl_2$ 2.5, $MgSO_4$ 1.2, $NaHCO_3$ 25, glucose 11; pH 7.4) equilibrated with a 5% $CO_2$ and 95% $O_2$. A latex balloon was passed into the left ventricle through the mitral valve and connected to a pressure transducer (Model p10EZ, Viggo-Spectramed, Calif.) and transducer amplifier and differentiator amplifier (Model 11-G4113-01, Gould Instrument System Inc., Ohio). After 30 minutes of stabilization, the balloon size was increased in 0.02 ml increments from 0.04 to a volume, at which end diastolic pressure was 30 mm Hg or more by the addition of saline. The systolic and diastolic pressures were recorded at each balloon volume and developed pressure was calculated as the difference between the systolic and diastolic pressures.

Measurement of left ventricular free wall remodeling: After function measurements, the hearts were fixed, sectioned, and traced onto a transparency. LVFW and scar sizes were quantified using computerized planimetry as described in the "Myocardial Scar Generation and Evaluation" section. The transplanted tissue size as a percentage of the scar size was similarly calculated.

Histological identification of transplanted muscle cells in the scar tissue: Fixed heart sections were embedded in paraffin, and cut into 10 µm thick sections. The sections were stained with hematoxylin and eosin as described in the "Histological Studies" section above.

Heart sections containing transplanted cells also were stained for myosin heavy chain (MHC) (Rougier Bio-Tech, Montreal). After deparaffination and rehydration, s samples were incubated for 30 minutes with a solution of 3% $H_2O_2$ in 70% methanol to inhibit endogenous myocardial peroxidase. Triton X-100 (0.2%) was used to treat samples for 10 minutes to enhance cell permeability. After blocking non-specific protein binding with 2% normal goat serum in 0.05 M Tris buffer (pH 7.4) for 15 minutes, primary antibodies against HCM (1:1000) were added and the samples were incubated at 37° C. for 30 minutes followed by an overnight incubation at 4° C. Negative control samples were incubated in PBS under the same conditions. After samples were washed with PBS, a biotin-labeled secondary antibody (1:250) was added and the samples were incubated at room temperature for 1 hour. After rinsing with PBS, the samples were exposed to an avidin-biotin complex conjugated with peroxidase at room temperature for 45 minutes. Visualization was performed with a diaminobenzidine solution (0.25 mg/ml in 0.05 Tris-HCl buffer containing 0.02% $H_2O_2$) for 10 minutes. The cellular nuclei were counter-stained with hematoxylin for 1 minute. The samples were covered and photographed.

Data Analysis: Data are expressed as the mean±standard error. The Statistical Analysis System software was used for all analysis (SAS Institute, Cary, N.C.). Comparisons of continuous variables between more than two groups were performed by a one-way analysis of variance. If the F ratio was significant from the ANOVA, a Duncan=s multiple-range t test was employed to specify differences between the groups. The critical alpha-level for these analyses was set at $p<0.05$.

Functional data were evaluated for the control and transplant groups by an analysis of covariance (ANCOVA) using intracavitary balloon volume as the covariate and systolic, diastolic and developed pressure as dependent variables. Main effects were group, volume, and the interaction between group and volume.

Results

Figure 6A:
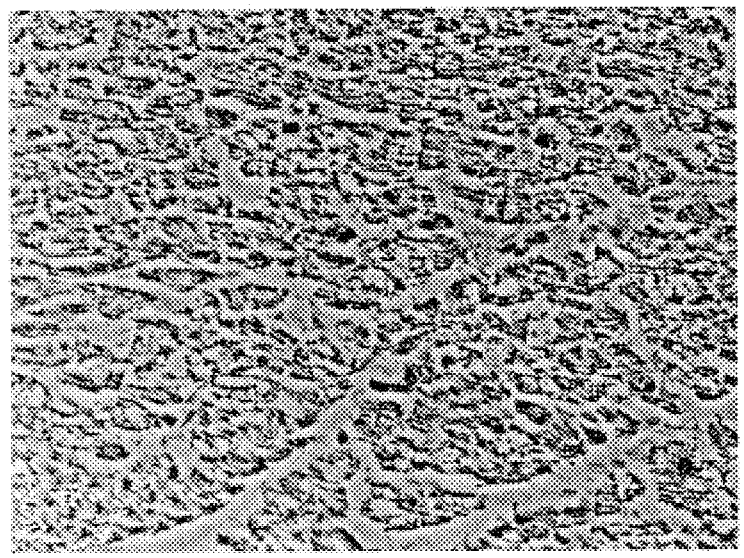
FIG. 6(A–D) shows photomicrographs of haematoxylin and eosin (H & E)-stained LVFW after cryo-injury. A) immediately after cryo-injury (magnification=200×), and B) 1 week (magnification=100×), C) 2 weeks (magnification=100×) D) 4 weeks (magnification=200×) after cryo-injury. The myocardium is fragmented immediately after cryo-injury. At 1 week, a predominantly mononuclear infiltrate is present and most of the necrosed cardiomyocytes have disappeared. At 2 weeks, fibroblasts and collagen are evident. The inflammatory infiltrate is almost gone. At 4 weeks, a transmural scar has formed.
Figure 6B:
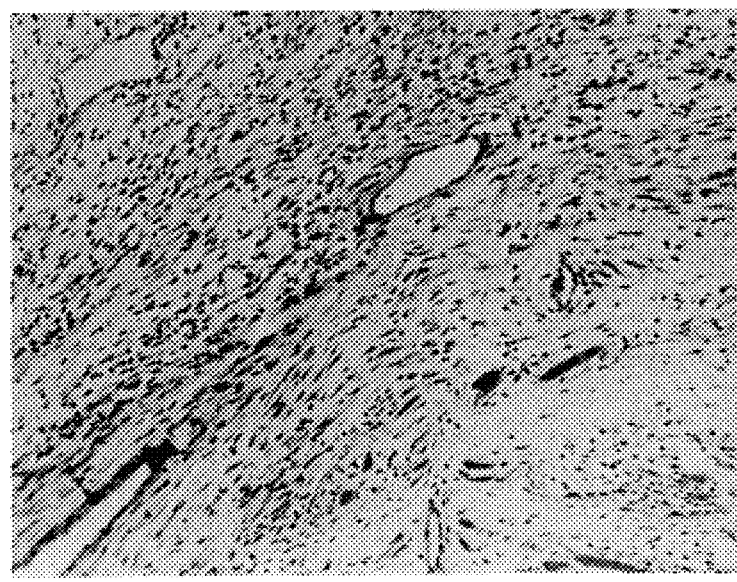
Figure 6C:
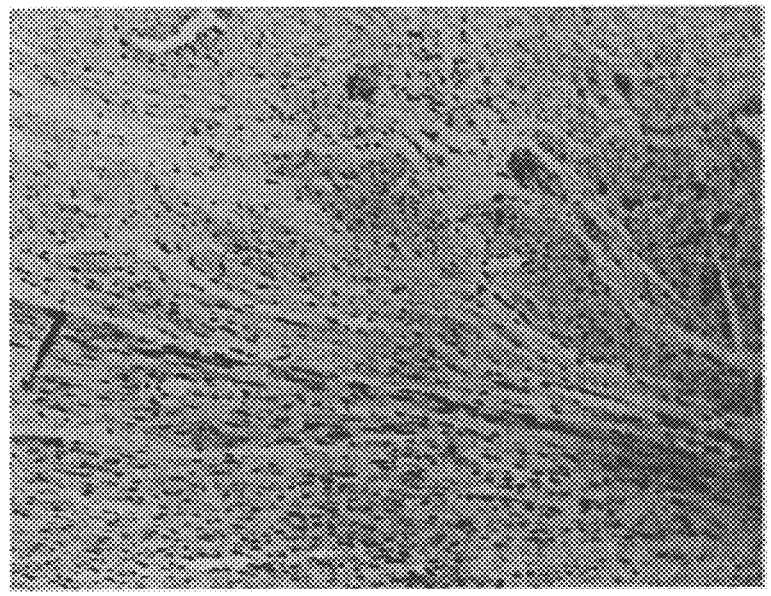
Figure 6D:
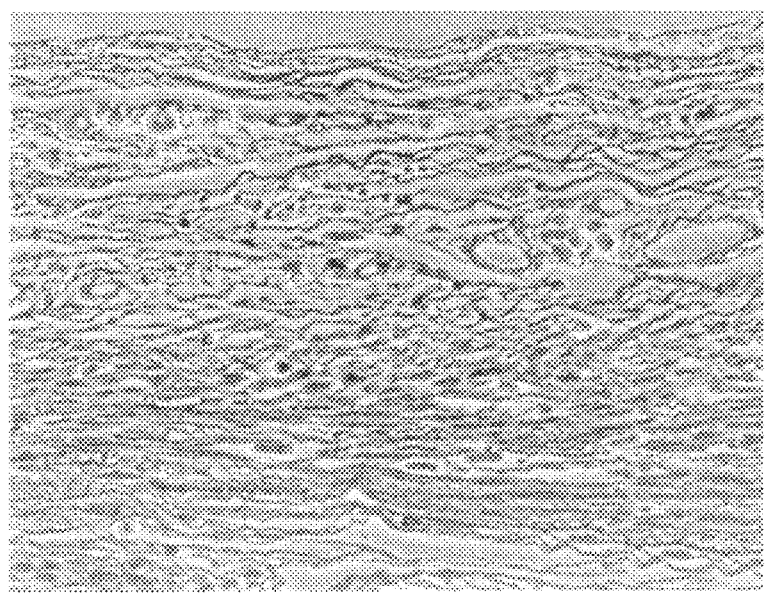
Figure 7A:
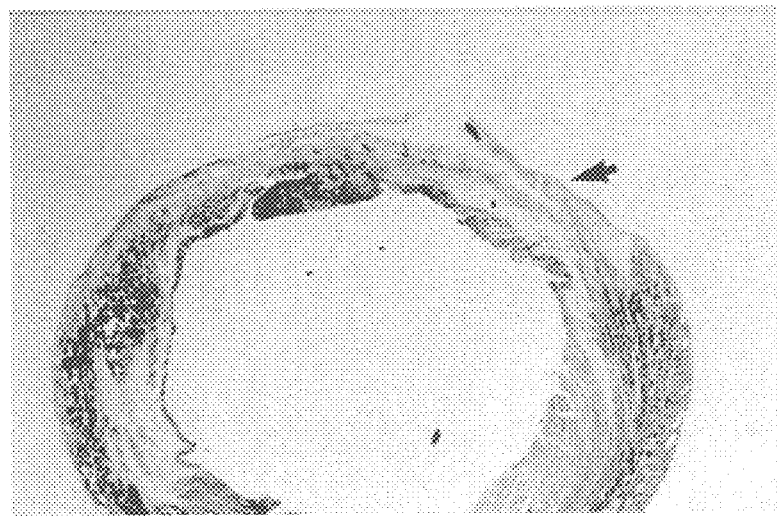
FIG. 7(A–D) shows photomicrographs of H & E-stained heart sections (5×) at A) 1, B) 2, C) 4, and D) 8 weeks after cryo-injury at LVFW. The size of the scar tissue (indicated by arrows) increases with time after injury.
Figure 7B:
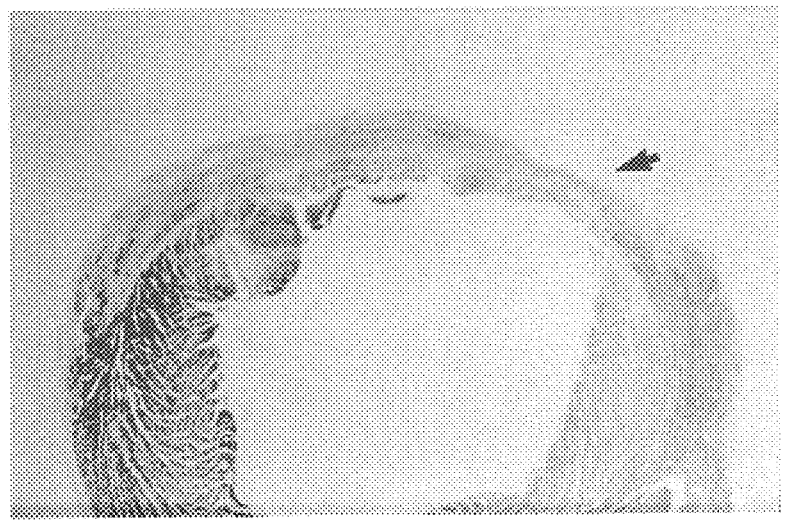
Figure 7C:
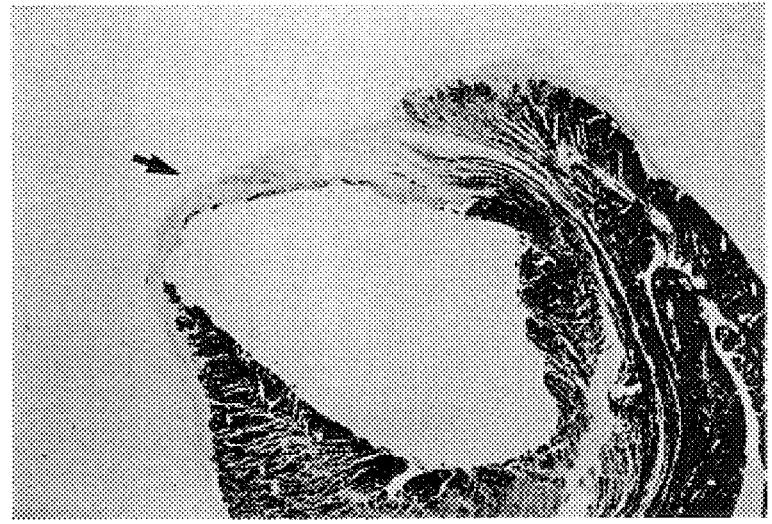
Figure 7D:
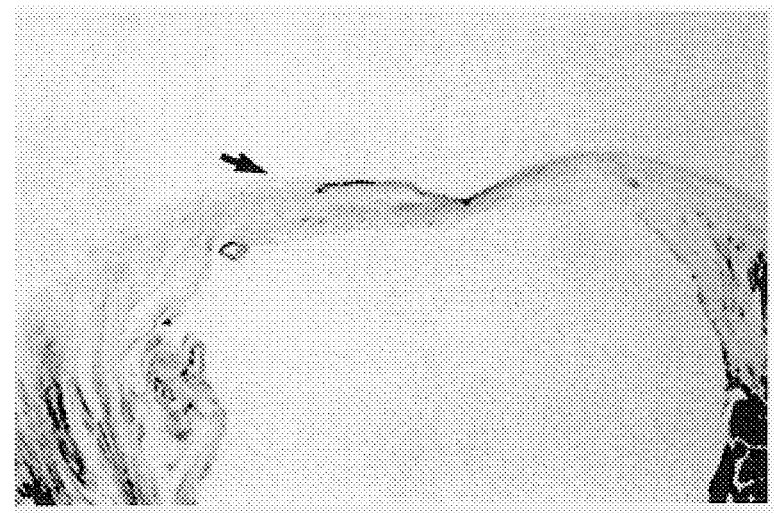

Histological and morphological changes of the hearts after myocardial injury: Immediately after cryo-injury, 25±3% of the size of the LVFW was transmurally damaged. The cardiomyocytes were fragmented (FIG. 6A). At one week, most of the necrosed cardiomyocytes were gone and a predominantly mononuclear inflammatory infiltrate was present in the affected area (FIG. 6B). At two weeks the inflammatory infiltrate had almost disappeared and fibroblasts and collagen deposition were evident (FIG. 6C). At four and eight weeks, the scar was composed of fibrotic tissue (FIG. 6D). The tissue was less cellular and lymphocytes were not observed.

Figure 8:
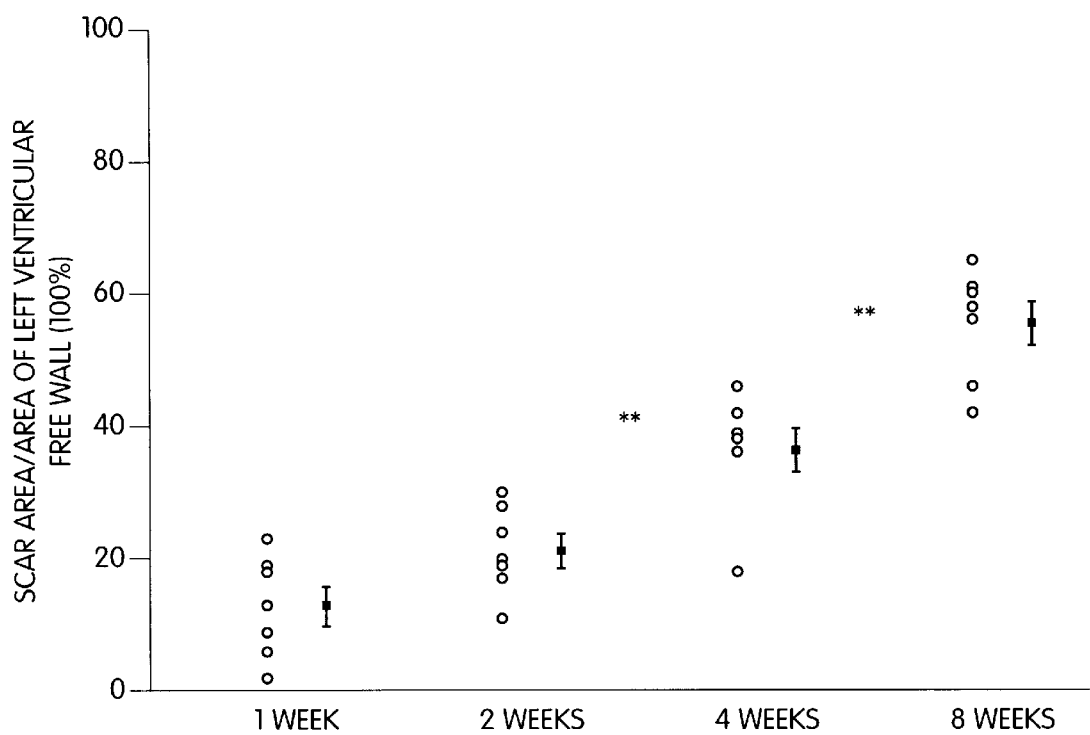
FIG. 8 is a graph showing percentages of scar tissue in the LVFW at 1 week, 2 weeks, 4 weeks, and 8 weeks after cryo-injury. The scar tissue size increased with time. Open circles represent individual scar sizes, and closed squares represent mean scar sizes ±SE (N=7). **p<0.01.
Figure 9A:
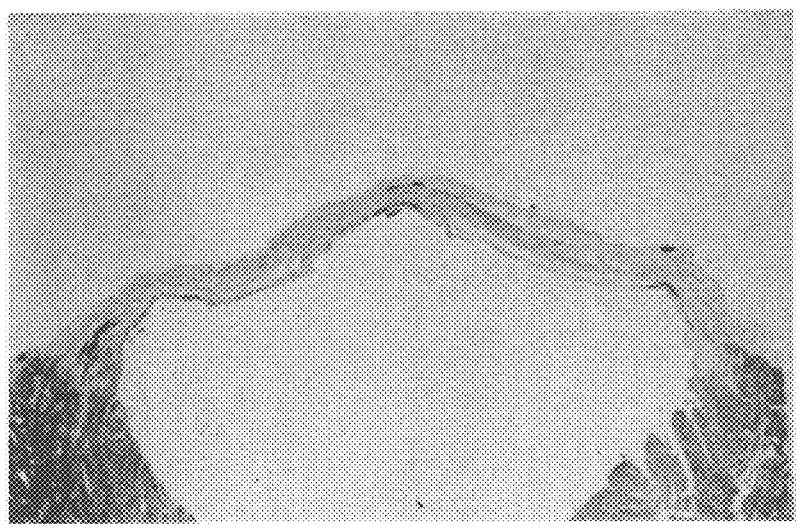
FIG. 9(A–D) shows photomicrographs of H & E-stained heart sections (5×) at 8 weeks after cryo-injury of the LVFW. The control heart (A) was transplanted with culture medium. Experimental hearts were transplanted with cultured fetal rat cardiomyocytes immediately (B), at 2 weeks (C) and at 4 weeks (D) after myocardial injury. Transplanted cardiac tissue was not observed in (A) and (B) hearts. Transplanted tissue (indicated by arrows) was found in myocardial scar tissue in (C) and (D) hearts. Host myocardium was usually present beneath the scar when the transplant was present, but never when the transplant was absent. We attribute the presence of the host myocardium to the cell transplant limiting scar expansion.
Figure 9B:
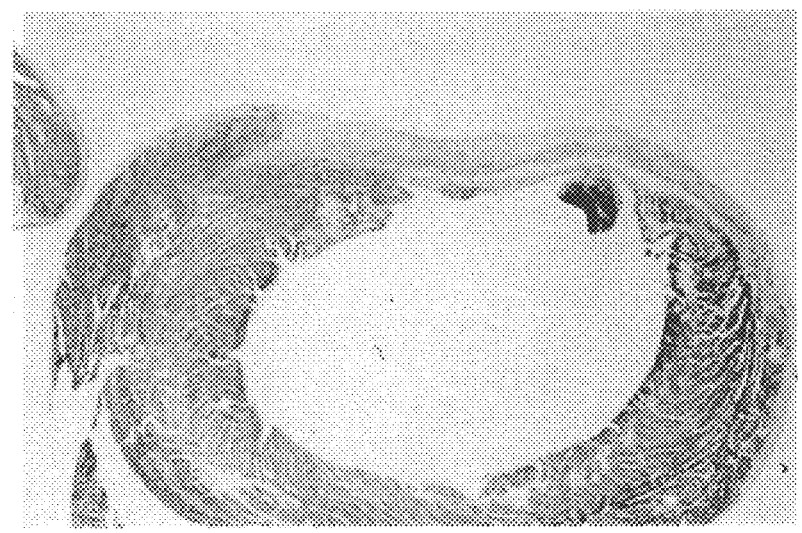
Figure 9C:
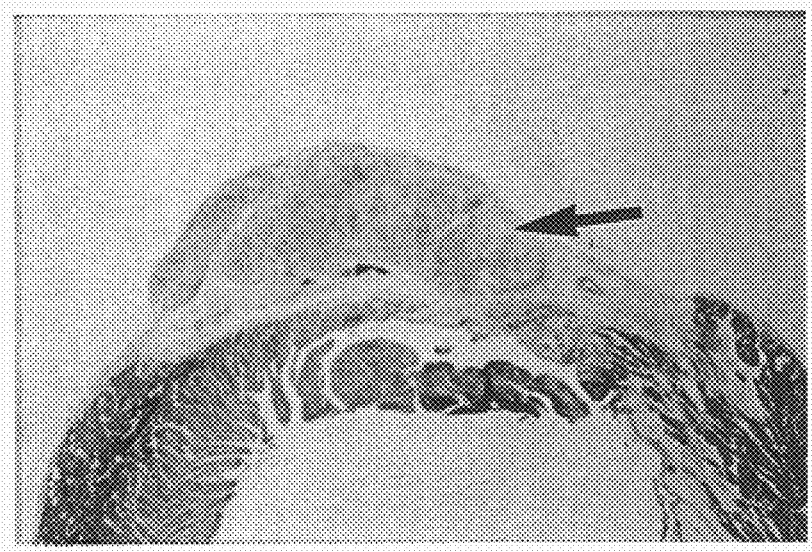
Figure 9D:
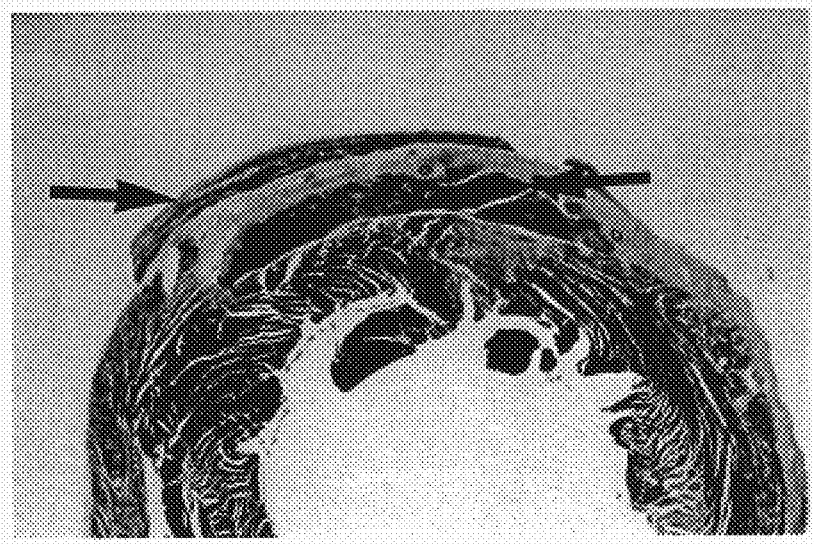

The myocardial scar size of the left ventricle expanded over the 8 week study period in the damaged hearts (FIGS. 7 and 8). Although the scar sizes at 1 and 2 weeks (13±6% and 21±4 of LVFW) were not statistically different, the size of 4-week-old scars (39±5% of LVFW) was larger ($p<0.01$). At 8 weeks there was a further increase ($p<0.01$) in scar size (55±3% of LVFW).

Although histological studies showed that the damage to newly-injuredmyocardium was transmural, some myocardium (12±5% of total scar area) was observed at the endocardium one week after myocardial injury (FIGS. 6 and 7). Lymphocytes surrounded the myocardium at this time. At 2 and 4 weeks, muscle tissue in the scar area (3±2% and 2±1.5% of total scar area) decreased dramatically ($p<0.01$) in size. At 8 weeks, the myocardial scar became transmural and there was no myocardium in the scar tissue.

Figure 10:
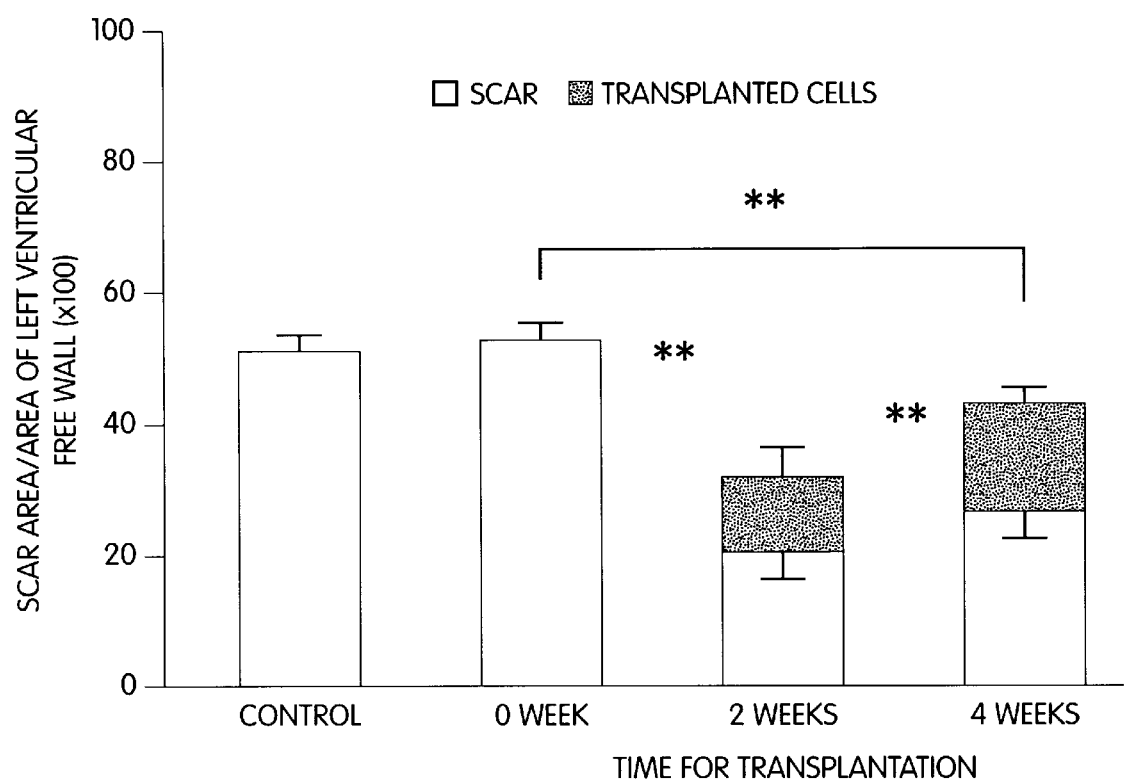
FIG. 10 is a graph showing percentages of scar tissue and transplanted cardiac tissue in the LVFW at 8 weeks after cryo-injury. Fetal rat cardiomyocytes transplanted at 2 and 4 weeks after myocardial injury formed cardiac tissues which occupied 34% and 31% of the total scar area, respectively. The cardiac transplant limited scar expansion. Results are expressed as mean ±SE. **p<0.01.
Figure 11:
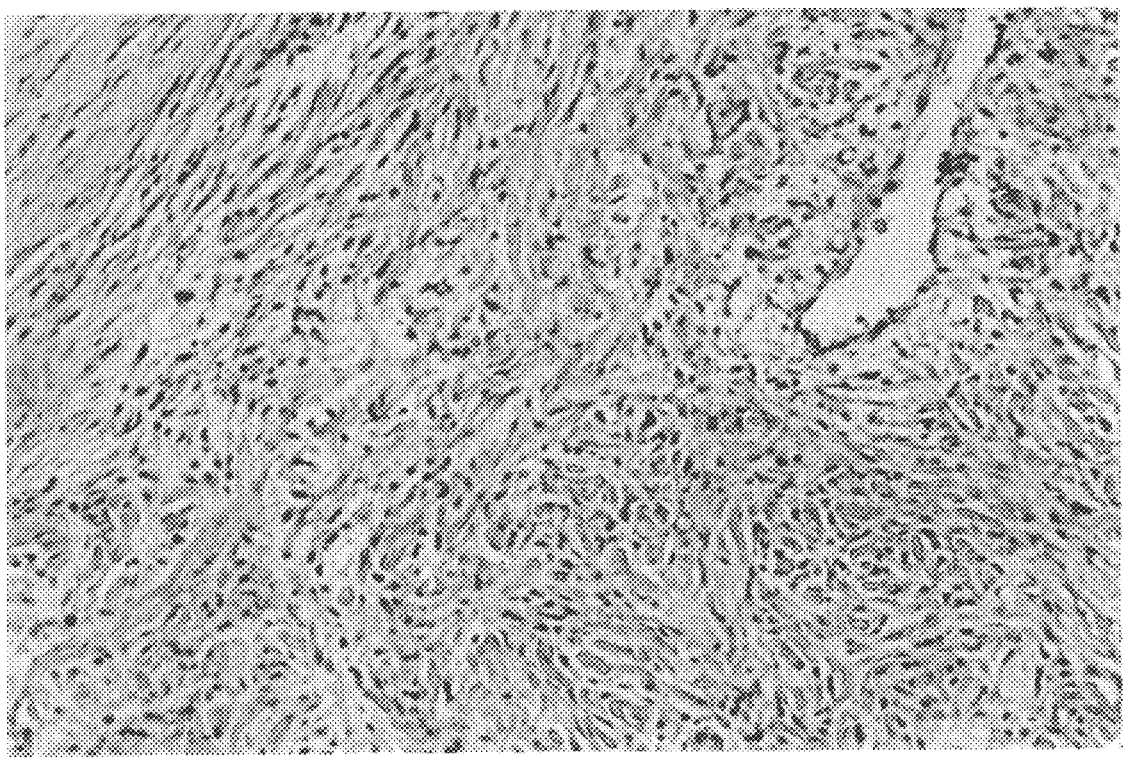
FIG. 11 shows a photomicrograph of fetal rat cardiomyocytes 6 weeks after transplantation (100×). The transplanted tissue stained positively (dark-brown color) for myosin heavy chain using the avidin-biotin-peroxidase complex technique.

Effect of transplanted cells on scar size: The fetal rat cardiomyocytes transplanted into myocardium immediately after myocardial damage did not survive in the transplanted area (FIGS. 9 and 10). The scar area (53±5%) of transplanted hearts was similar to that of the control group 55±3% of the LVFW. There was no cardiac tissue at endocardial area. Cardiomyocytes transplanted at 2 weeks after myocardial damage formed cardiac tissue which stained positively for myosin heavy chain (FIG. 11). The newly formed cardiac tissue occupied 34% of the total scar area (11±3% of the LVFW). Similarly cardiomyocytes transplanted at 4 weeks occupied 31% of total scar area (12±2% of LVFW).

In addition to the cardiac tissue formed by transplanted cardiomyocytes, recipient myocardium was also found at endocardium in both transplanted groups. The scar sizes for both the 2 and 4 week hearts transplanted with cells were smaller ($p<0.01$) than the scar size of the control (nontransplantable) hearts. The scar size of the hearts transplanted at 2 weeks (32±5%) was smaller ($p<0.01$) than that of the hearts transplanted at 4 weeks (42±2%) (FIG. 10).

Figure 12:
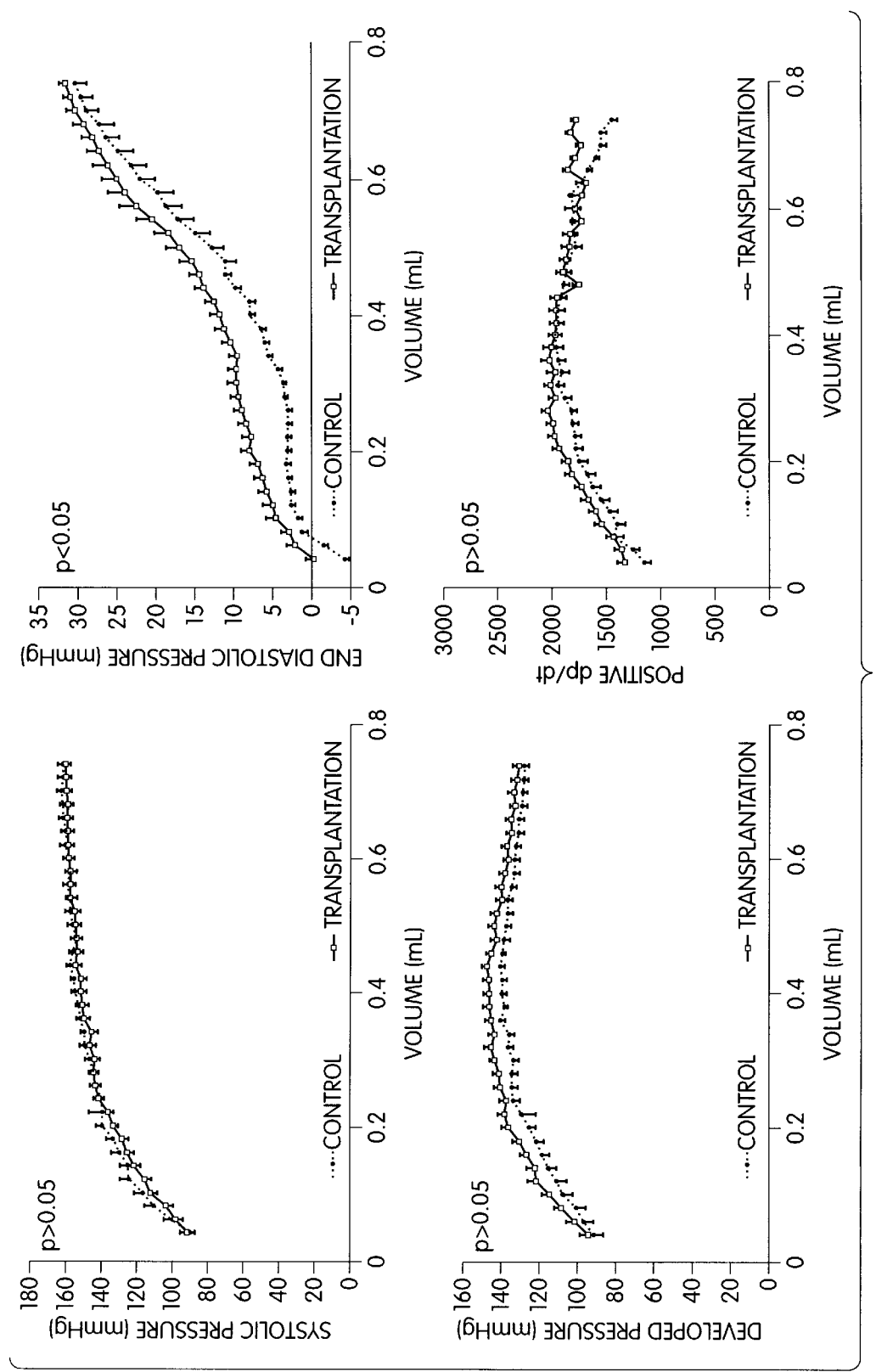
FIG. 12 shows graphs of systolic, diastolic, developed balloon pressures and positive dp/dt of control and transplanted hearts with increasing balloon volumes. Fetal rat cardiomyocytes were transplanted immediately after myocardial injury. There were no differences in systolic and developed pressures between the transplanted and control hearts. Results are expressed as mean ±SE (N=8). Closed circles represent control hearts; open squares represent transplanted hearts.
Figure 13:
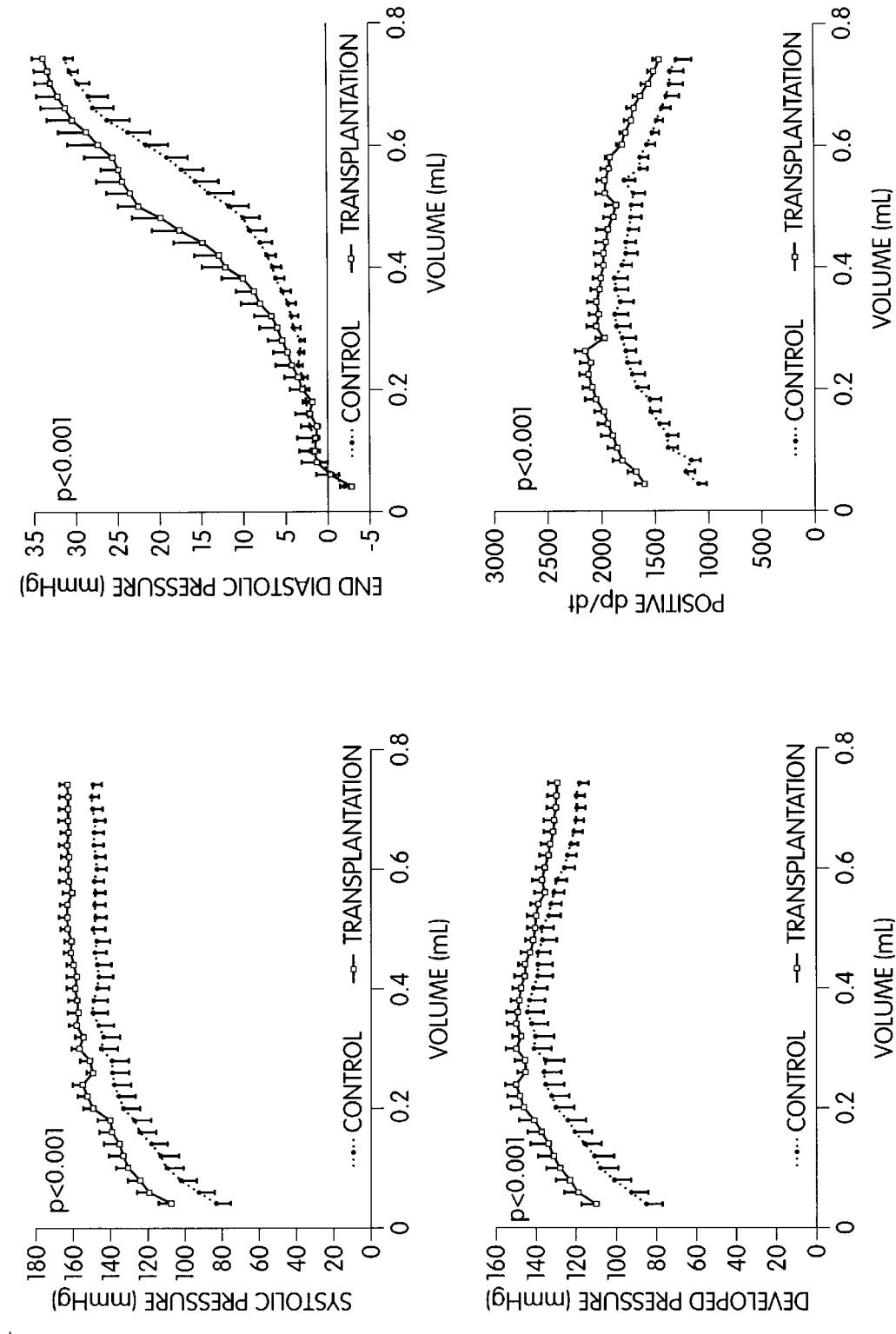
FIG. 13 shows graphs of systolic, diastolic, developed balloon pressures and positive dp/dt of control and transplanted hearts with increasing balloon volumes. Transplantation was performed at 2 weeks after myocardial injury. Systolic and developed pressures of the transplanted rat hearts were greater (p<0.01) than those of the control hearts. Results are expressed as mean ±SE (N=8). Closed circles represent control hearts; open squares represent transplanted hearts.

Effect of transplanted cells on heart function: When cardiomyocytes were transplanted immediately after myocardial injury, ventricular function of hearts transplanted with cells was similar to that of control (nontransplanted) hearts (FIG. 12). An analysis of covariance demonstrated no association between the control group and the treatment group for developed pressures. When the cardiomyocytes were transplanted at 2 weeks after myocardial injury, the transplanted hearts had better ($p=0.001$) ventricular function than the control hearts (FIG. 13). Similar diastolic and developed pressures were found at lower balloon volumes in the transplant group.

Figure 14:
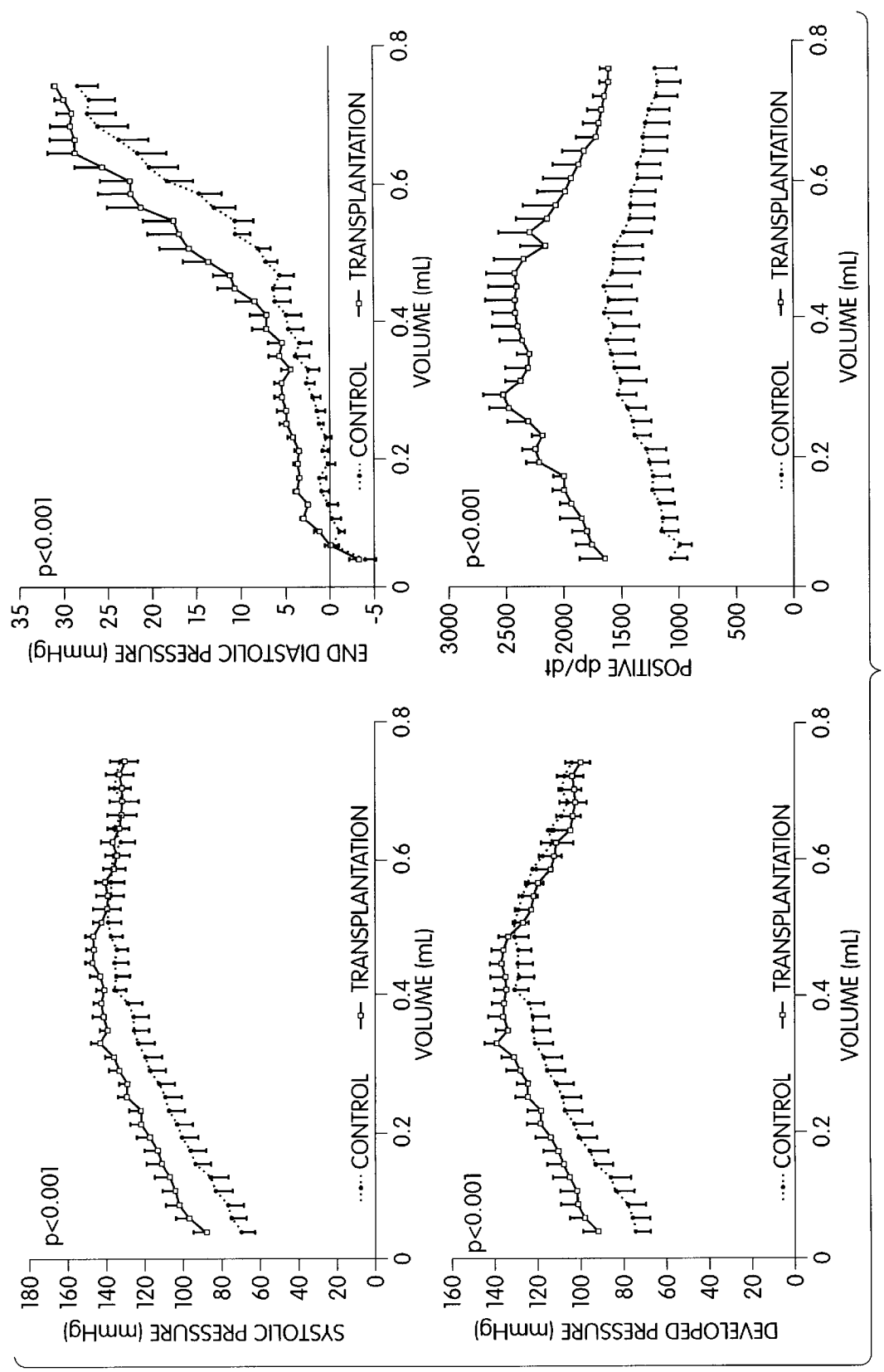
FIG. 14 shows graphs of systolic, diastolic, developed balloon pressures and positive dp/dt of control and transplanted hearts with increasing balloon volumes. Transplantation was performed at 4 weeks after myocardial injury. Systolic and developed pressures of the transplanted rat hearts were significantly greater than those of control hearts (p<0.01). Results are expressed as mean ±SE (N=12). Closed circles represent control hearts; open squares represent transplanted hearts.
Figure 15:
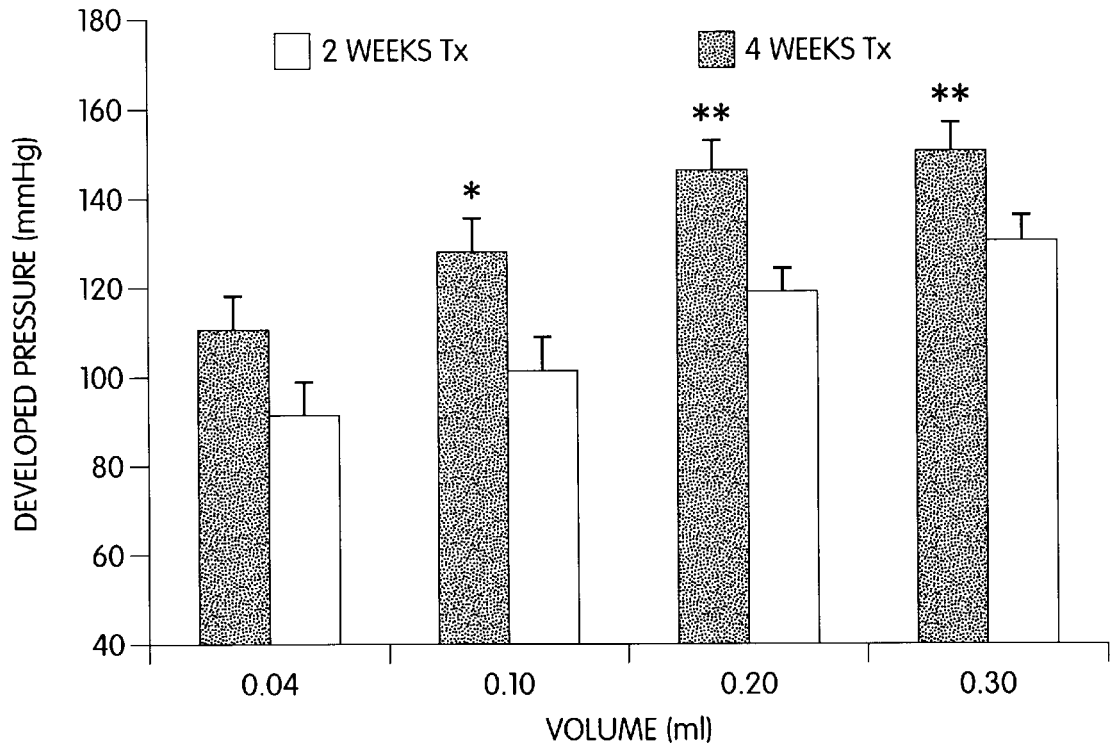
FIG. 15 is a graph showing developed pressures at balloon volumes of 0.04, 0.1, 0.2 and 0.3 ml of the hearts transplanted with fetal cardiomyocytes at 2 and 4 weeks after myocardial injury. The developed pressures of hearts transplanted at 2 weeks were significantly higher than those of the hearts transplanted at 4 weeks. Results are expressed as mean ±SE. *p<0.05, **p<0.01.

Cardiomyocytes transplanted at 4 weeks after myocardial injury also improved ($p<0.001$) myocardial function (FIG. 14). FIG. 15 shows that hearts transplanted at 2 weeks had higher developed pressures at balloon volumes 0.1 ml ($p<0.05$), 0.2 ml ($p<0.01$) and 0.3 ml ($p<0.01$) than hearts transplanted at 4 weeks.

The transplant tissue visibly contracted, but at different rates than did host myocardium. The contraction of the transplanted tissue persisted after dissection of the recipient heart, but its rate of contraction continued to be different.

In the rat, loss of necrosed ventricular tissue occurs by 2 days after cyro-injury of the myocardium. At this time there is an acute inflammatory reaction with neutrophils accumulating first in the periphery and later in the center of the necrotic region. A chronic inflammatory reaction involving macrophages and lymphocytes follows the acute reaction.

One week after cryo-injury, more than 80% necrotic muscle fibres had disappeared. The remaining muscle fibres were surrounded by lymphocytes.

The inflammatory reaction is less intense two weeks after cryo-injury (and is absent by three weeks): two weeks after cryo-injury, the scars of the control animal hearts showed minimal or no inflammatory reaction. Two-week-old scars were less mature and contained more blood vessels and fibroblasts than 4-week-old scars, which comprised firm connective tissue. Compared to one-week-old scars, there was less cardiac tissue in older scars. It is possible that progressive inflammation and lack of oxygen and nutrient supply decreased the myocardial tissue over time.

The cardiomyocytes transplanted immediately after cryo-injury did not survive in any of the animals studied. We believe the activated neutrophils and macrophages in the inflamed scar area destroyed the transplanted cells. At 8 weeks, the left ventricular chamber of the animals transplanted at the time of cryo-necrosis was similar to that of the control scar. The chamber was dilated due to thinning of the scar. The remaining viable muscle of the left ventricle was hypertrophied. No inflammatory reaction was seen. The function of these transplanted hearts was similar to that of the control hearts.

All the animals transplanted with the fetal cardiomyocytes at 2 and 4 weeks formed cardiac tissue within the scar tissue; therefore, transplantation is possible in both the immature and mature scar. Histological studies of the LVFW of the transplanted hearts showed that host myocardium was usually present beneath the scar when the transplant was present. This did not occur when the transplant was absent.

Control scar studies showed that scars were always transmural and did not have s host cardiomyocytes underneath. Scar sizes and left ventricular chamber sizes of the hearts transplanted at 2 weeks were smaller than those of hearts transplanted at 4 weeks. In turn, scar sizes and left ventricular chamber sizes of the hearts transplanted at 4 weeks were smaller than those of the control hearts. Consistent with these histological findings, the myocardial function of the hearts transplanted at 2 weeks was better than that of the hearts transplanted at 4 weeks. We attributed the improved myocardial function to less ventricular dilatation and scar thinning. Compared with the sham-operated animals in our previous study, the contractile function of the hearts transplanted at 2 weeks was less efficient. Transplantation as soon as possible after the acute inflammatory reaction in the infarcted myocardium has disappeared should minimize ventricular remodeling and optimize myocardial function.

Although the mechanism of improved heart function is unknown, a cardiomyocyte transplant forms the equivalent of a viable epicardial rim and prevents ventricular dilatation and over-stretching of the cardiomyocytes during systole. With over-stretching of the cardiomyocytes, cardiac function is diminished (Frank-Starling Law). The elastic properties of the contractile apparatus of the transplanted cardiomyocytes may prevent host fibroblast and cardiomyocyte stretching and ventricular enlargement.

In the course of forming cardiac tissue from transplanted cardiomyocytes, angiogenesis occurred. Angiogenesis is most likely necessary to maintain the viability of the transplanted muscle cells. However, an increased blood supply in the scar could also facilitate fibroblast turnover and strengthening of the scar in response to left ventricular free wall stretch.

With the advent of thrombolysis and percutaneous transluminal coronary angioplasty (PTCA), the incidence of patchy nontransmural infarction is becoming more frequent and transmural infarction with aneurysm formation less common. If the blood flow to the viable cardiomyocytes within the ventricular scar is insufficient for contractile function, stimulation of angiogenesis in the scar tissue becomes important. With adequate blood flow, normal contractile function should return to the hibernating cardiomyocytes within the scar. Transplantation of fetal cardiomyocytes could offer significant benefits to the patients with a patchy infarction. Angiogenesis would be stimulated in the scar, increase the blood flow, and restore normal contractile function to the host's hibernating cardiomyocytes. The transplanted cardiomyocytes should also increase the contractile capacity of the scar tissue and decrease the contractile requirements of the non-affected host myocardium. Patients with angina that cannot be corrected by bypass surgery may benefit from angiogenesis secondary to cardiomyocyte transplantation. In addition, it may be beneficial to stimulate angiogenesis with growth factors prior to autotransplantation.

In summary, transplantation of fetal cardiomyocytes form cardiac tissue in scar tissue which limits ventricular dilatation and scar thinning. The optimal time for transplantation for improved myocardial function is after the acute inflammatory reaction and before significant ventricular dilatation has occurred.

CO-IMPLANTATION OF ENDOTHELIAL CELLS WITH ADULT CARDIOMYOCYTES IMPROVES THE FUNCTION OF INFARCTED HEARTS

Cardiac transmural scars were induced by cryo-injury in the left ventricular free wall (LVFW) of Sprague-Dawley rat hearts, as described in the previous examples. Three weeks after cryo-injury, the rats were divided into three groups (eight rats per group), and cardiac transmural scars were transplanted with either medium (no cells), adult cardiomyocytes alone, or adult cardiomyocytes plus endothelial cells. Cardiac function was assessed using a Langandorff preparation five weeks after cell transplantation (Stephen et al., *Annals of Thoracic Surgery* 59: 1127–1133, 1995).

Figure 16:
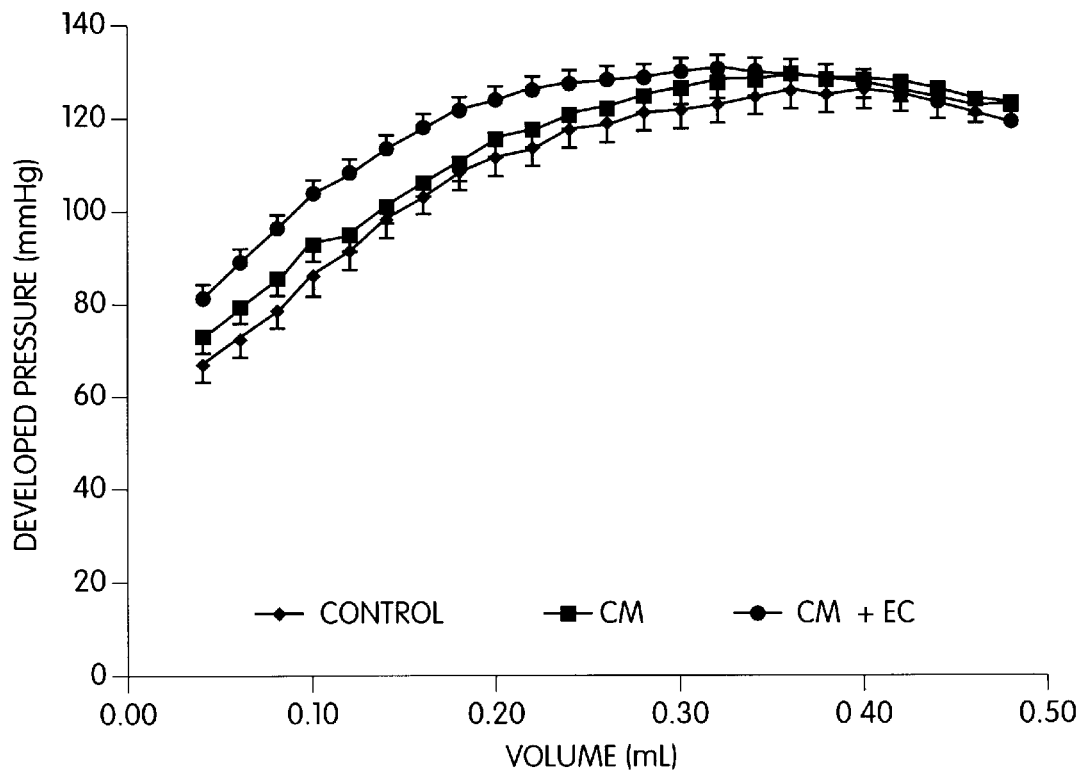
FIG. 16 is a graph showing developed pressure in cryo-injured hearts containing transmural scars transplanted with medium (control), adult cardiomyocytes (CM) or adult cardiomyocytes plus vascular endothelial cells (CM+EC).

FIG. 16 shows a graph of developed pressure in infarcted rat hearts injected with either medium (negative control), adult cardiomyocytes alone (CM), or adult cardiomyocytes plus endothelial cells (CM+EC). Adult cardiomyocytes injected alone formed tissue within the ventricular scar, but did not improve cardiac function, compared to hearts injected with medium alone. In contrast, injection of adult cardiomyocytes plus endothelial cells significantly improved cardiac function (p<0.01), compared to hearts injected with medium or cardiomyocytes alone. Co-injection of endothelial cells likely stimulates angiogenesis, which enhances survival of adult cardiomyocytes.

Although the invention has been described with reference to certain specific embodiments, various modifications thereof will be apparent to those skilled in the art without departing from the spirit and scope of the invention as outlined in the claims appended hereto.

What is claimed is:

1. Isolated cells, said cells comprising at least one of the following cell types:
    adult cardiomyocytes;
    pediatric cardiomyocytes;
    adult fibroblasts;
    fetal fibroblasts;
    adult smooth muscle cells;
    fetal smooth muscle cells;
    endothelial cells; or
    skeletal myoblasts,
wherein said cells survive in myocardial scar tissue after transplantation into said myocardial scar tissue, and wherein said cells improve cardiac function, relative to cardiac function of a heart having similar myocardial scar tissue that is not transplanted with said cells, wherein cardiac function is assessed by at least one of the criteria selected from the group consisting of: area occupied by said scar tissue; vascularization of said scar tissue; blood flow to said scar tissue; developed pressure; systolic pressure; end diastolic pressure; and $\Delta$Pressure/$\Delta$time.

2. The cells of claim 1, wherein said cells comprise at least two different cell types.

3. The cells of claim 2, wherein said cells comprise a combination of:
    adult cardiomyocytes and endothelial cells;
    pediatric cardiomyocytes and endothelial cells; or
    myoblasts and endothelial cells.

4. A method of forming a stable cardiac graft in a mammal, said method comprising transplanting, into the scar tissue of a heart, cells comprising at least one of the following cell types:
    adult cardiomyocytes;
    pediatric cardiomyocytes;
    adult fibroblasts;
    fetal fibroblasts;
    adult smooth muscle cells;
    fetal smooth muscle cells;
    endothelial cells; or
    skeletal myoblasts,
wherein said cells survive in scar tissue in a heart after transplantation into said scar tissue, and wherein said cells improve cardiac function, relative to cardiac function of a heart having similar myocardial scar tissue that is not transplanted with said cells, wherein cardiac function is assessed by at least one of the criteria selected from the group consisting of: area occupied by said scar tissue; vascularization of said scar tissue; blood flow to said scar tissue; developed pressure; systolic pressure; end diastolic pressure; and $\Delta$Pressure/$\Delta$time, wherein at least 10% of said scar tissue is occupied by transplanted cells four weeks after transplantation.

5. The method of claim 4, wherein said cells include at least two different cell types.

6. The method of claim 4, wherein said cells for transplantation comprise a combination of:
    adult cardiomyocytes and endothelial cells;
    pediatric cardiomyocytes and endothelial cells; or
    myoblasts and endothelial cells.

7. The method of claim 5, wherein growth factors are co-transplanted with said cells.

8. The method of claim 7, wherein said growth factors are chosen from the group consisting of: insulin-like growth factors I and II; transforming growth factor-$\beta$1; platelet-derived growth factor-B; basic fibroblast growth factor; and, vascular endothelial growth factor.

9. A method of treating defective, damaged or scarified heart tissue, said method comprising transplanting into said defective, damaged or scarified heart tissue a graft of cells, wherein said graft of cells comprises a combination of:
    adult cardiomyocytes and endothelial cells;
    pediatric cardiomyocytes and endothelial cells; or
    myoblasts and endothelial cells.

10. The method of claim 9, wherein said graft is used for cardiomyoplasty.

11. The method of claim 9, wherein said graft is used for closing cardiac defects.

12. The method of claim 9, wherein said graft is used for myocardial reconstructive surgery.

13. A therapeutic graft for implantation in mammalian myocardial tissue or scar tissue in a heart, said graft comprising biodegradable or non-biodegradable scaffolding supporting cells, wherein said cells comprise a combination of:
    adult cardiomyocytes and endothelial cells;
    pediatric cardiomyocytes and endothelial cells; or
    myoblasts and endothelial cells.

14. The graft of claim 13, wherein said scaffolding comprises Dacron or polyglycolic acid polymers with or without polylactic acid polymers.

15. The graft of claim 13, wherein said graft further includes an implantable pacemaker.

16. The graft of claim 13, wherein said cells are transfected to deliver recombinant molecules to said myocardial tissue or scar tissue.

17. The graft of claim 13, further comprising growth factors.

18. The graft of claim 17, wherein said growth factors are chosen from the group consisting of: insulin-like growth factors I and II; transforming growth factor-β1; platelet-derived growth factor-B; basic fibroblast growth factor; and, vascular endothelial growth factor.

19. The graft of claim 13, wherein said cells are suspended on a biodegradable mesh.

20. A therapeutic graft for use in scar tissue in a mammalian heart, said graft comprising transplanted cells, wherein said cells comprise:

adult cardiomyocytes;

adult fibroblasts;

fetal fibroblasts;

smooth muscle cells;

endothelial cells; or skeletal myoblasts.

21. A therapeutic graft for use in myocardial tissue in a mammalian heart, said graft comprising transplanted cells, wherein said transplanted cells comprise:

adult fibroblasts;

fetal fibroblasts;

smooth muscle cells; or endothelial cells.

22. A method of forming a stable myocardial graft in a mammal, said method comprising transplanting cells into myocardial tissue in the heart of said mammal, wherein said cells comprise:

adult fibroblasts;

fetal fibroblasts;

smooth muscle cells; or endothelial cells.

23. A method of treating defective, damaged or scarified heart tissue, said method comprising transplanting, into said tissue, a graft of cells comprising:

adult cardiomyocytes;

adult fibroblasts;

fetal fibroblasts;

smooth muscle cells;

endothelial cells; or skeletal myoblasts.

* * * * *